US009801911B2

(12) United States Patent
Tang et al.

(10) Patent No.: US 9,801,911 B2
(45) Date of Patent: Oct. 31, 2017

(54) EXPANSION OF ALLOANTIGEN-REACTIVE REGULATORY T CELLS

(71) Applicant: THE REGENTS OF THE UNIVERSITY OF CALIFORNIA, Oakland, CA (US)

(72) Inventors: Qizhi Tang, San Francisco, CA (US); Jeffrey A. Bluestone, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 222 days.

(21) Appl. No.: 14/382,537

(22) PCT Filed: Mar. 1, 2013

(86) PCT No.: PCT/US2013/028734
§ 371 (c)(1),
(2) Date: Sep. 2, 2014

(87) PCT Pub. No.: WO2013/131045
PCT Pub. Date: Sep. 6, 2013

(65) Prior Publication Data
US 2015/0110761 A1    Apr. 23, 2015

Related U.S. Application Data

(60) Provisional application No. 61/606,329, filed on Mar. 2, 2012.

(51) Int. Cl.
| C12N 5/071 | (2010.01) |
| C12N 5/00 | (2006.01) |
| C12N 5/02 | (2006.01) |
| A61K 35/17 | (2015.01) |
| A61K 31/436 | (2006.01) |
| A61K 31/5377 | (2006.01) |
| A61K 31/573 | (2006.01) |
| C12N 5/0783 | (2010.01) |
| A61K 39/00 | (2006.01) |
| C12N 5/0781 | (2010.01) |

(52) U.S. Cl.
CPC ............ *A61K 35/17* (2013.01); *A61K 31/436* (2013.01); *A61K 31/5377* (2013.01); *A61K 31/573* (2013.01); *A61K 39/001* (2013.01); *C12N 5/0635* (2013.01); *C12N 5/0637* (2013.01); *C12N 2501/04* (2013.01); *C12N 2501/2304* (2013.01); *C12N 2501/515* (2013.01); *C12N 2502/1107* (2013.01); *C12N 2502/30* (2013.01)

(58) Field of Classification Search
None
See application file for complete search history.

(56) References Cited

U.S. PATENT DOCUMENTS

| 5,540,926 A | 7/1996 | Aruffo et al. |
| 6,670,146 B2 | 12/2003 | Barrat et al. |
| 6,746,670 B2 | 6/2004 | Levings et al. |
| 6,759,035 B2 | 7/2004 | Horwitz |
| 7,494,812 B2 | 2/2009 | Zadeh |
| 7,541,184 B2 | 6/2009 | Berenson et al. |
| 7,572,631 B2 | 8/2009 | Berenson et al. |
| 7,651,855 B2 | 1/2010 | Blazar et al. |
| 7,722,862 B2 | 5/2010 | Bluestone et al. |
| 7,745,140 B2 | 6/2010 | June et al. |
| 7,771,932 B1 | 8/2010 | Groux et al. |
| 2008/0131445 A1 | 6/2008 | Bluestone et al. |
| 2009/0324557 A1 | 12/2009 | Tu et al. |

FOREIGN PATENT DOCUMENTS

| WO | 2009/073599 A1 | 6/2009 |
| WO | 2010/129770 A1 | 11/2010 |

OTHER PUBLICATIONS

Jiang et al. 2003, Blood. vol. 102: 2180-2186.*
Getnet et al., 2010, Mol. Immunol. vol. 47: 1595-1600.*
Mason et al., 2008, Gene Ther. vol. 15: 955-965.*
Bluestone et al., "Therapeutic Vaccination using CD4+ CD25+ Antigen-Specific Regulatory T Cells", Proc Natl Acad Sci, USA, vol. 101(Suppl. 2), 2004, pp. 14622-14626.
Brennan et al., "Requirements for Prolongation of Allograft Survival with Regulatory T Cell Infusion in Lymphosufficient Hosts", J Surg Res, vol. 169, 2011, pp. e69-e75.
Chen et al., "Direct Expansion of Human Allospecific FoxP3+ CD4+ Regulatory T Cells with Allogeneic B Cells for Therapeutic Application", J Immunol, vol. 183, 2009, pp. 4094-4102.
Fan et al., "Comparative Study of Regulatory T Cells Expanded ex Vivo from Cord Blood and Adult Peripheral Blood", Immunology, vol. 136, 2012, pp. 218-230.
Hoffmann et al. , "Large-Scale in Vitro Expansion of Polyclonal Human CD4+ CD25 high Regulatory T Cells", Blood, vol. 104, 2004, pp. 895-903.
Iikuni et al., "Cutting Edge: Regulatory T Cells Directly Suppress B Cells in Systemic Lupus Erythematosus", J Immunol, vol. 183, 2009, pp. 1518-1522.
Kang et al., "CD4+CD25+Regulatory T Cells in Transplantation: Progress Challenges and Prospects", Am J Transplant, vol. 7, 2007, pp. 1457-1463.

(Continued)

Primary Examiner — Amy Juedes
(74) Attorney, Agent, or Firm — Morrison & Foerster LLP

(57) ABSTRACT

The present disclosure relates generally to the manufacture of regulatory T cells (Tregs) for use in immunotherapy. In particular, the present disclosure relates to robust approaches for the expansion of alloantigen-reactive Tregs ex vivo. Alloantigen-reactive Tregs produced in this way are suitable for the induction and/or maintenance of immunologic tolerance in recipients of allogeneic transplants.

9 Claims, 12 Drawing Sheets

(56) References Cited

OTHER PUBLICATIONS

Kessel et al., "Human CD19+ CD25high B Regulatory Cells Suppress Proliferation of CD4+ T Cells and Enhance Foxp3 and CTLA-4 Expression in T-Regulatory Cells", Autoimmunity Reviews, vol. 11, 2012, pp. 670-677.

Park et al., "Enhancement of Proliferation and Antigen Presentation of Human B Cells in Vitro by K562 Cells Expressing CD40L", Immune Network, vol. 7, 2007, pp. 80-86.

Putnam et al., "Expansion of Human Regulatory T-Cells from Patients with Type 1 Diabetes", Diabetes, vol. 58, 2009, pp. 652-662.

Putnam et al., "Clinical Grade Manufacturing of Human Alloantigen-Reactive Regulatory T Cells for Use in Transplantation", Am J Transplant, vol. 13, 2013, pp. 3010-3020.

Raimondi et al., "Mammalian Target of Rapamycin Inhibition and Alloantigen-Specific Regulatory T Cells Synergize to Promote Long-Term Graft Survival in Immunocompetent Recipients", J Immunol, vol. 184, 2010, pp. 624-636.

Tang et al., "CD4+ Foxp3+ Regulatory T Cell Therapy in Transplantation", J Mol Cell Biol, vol. 4, 2011, pp. 11-21.

Tang et al., "Regulatory T-Cell Therapy in Transplantation: Moving to the Clinic", Cold Spring Harbor Perspectives in Medicine, vol. 3, 2013, pp. 1-15.

Tang et al., "The Foxp3+ Regulatory T Cell: A Jack of all Trades, Master of Regulation", Nat Immunol., vol. 9, 2008, pp. 239-244.

Trenado et al., "Ex Vivo-Expanded CD4+ CD25+ Immunoregulatory T Cells Prevent Graft-Versus-Host-Disease by Inhibiting Activation/Differentiation of Pathogenic T Cells", J Immunol, vol. 176, 2006, pp. 1266-1273.

Tu et al., "Efficient Generation of Human Alloantigen-Specific CD4+ Regulatory T Cells from Naive Precursors by CD40-Activated B Cells", Blood, vol. 112, 2008, pp. 2554-2562.

Zheng et al., "Efficient Induction and Expansion of Human Alloantigen-Specific CD8 Regulatory T Cells from Naive Precursors by CD40-Activated B Cells", J Immunol, vol. 183, 2009, pp. 3742-3750.

European Office Action received for European Patent Application No. 13754740.2, dated Jul. 15, 2016, 4 pages.

Extended European Search Report received for European Patent Application No. 13754740.2, dated Jun. 30, 2015, 7 pages.

International Preliminary Report on Patentability received for PCT Application No. PCT/US2013/028734, dated Sep. 12, 2014, 7 pages.

International Search Report and Written Opinion received for PCT Patent Application No. PCT/US2013/028734, dated Jun. 27, 2013, 8 pages.

Allan et al., "Activation-Induced FOXP3 in Human T Effector Cells does not Suppress Proliferation or Cytokine Production", International Immunology, vol. 19, 2007, pp. 345-354.

Baron et al., "DNA Demethylation in the Human FOXP3 Locus Discriminates Regulatory T Cells from Activated FOXP3+ Conventional T Cells", European Journal of Immunology, vol. 37, 2007, pp. 2378-2389.

Haribhai et al., "A Requisite Role for Induced Regulatory T Cells in Tolerance based on Expanding Antigen Receptor Diversity", Immunity, vol. 35, 2011, pp. 109-122.

Liu et al., "CD127 Expression Inversely Correlates with FoxP3 and Suppressive Function of Human CD4+ T Reg Cells", Journal of Experimental Medicine, vol. 203, 2006, pp. 1701-1711.

Miyao et al., "Plasticity of Foxp3+ T Cells Reflects Promiscuous Foxp3 Expression in Conventional T Cells but Not Reprogramming of Regulatory T Cells", Immunity, vol. 36, 2012, pp. 262-275.

Morgan et al., "Expression of FOXP3 mRNA is not Confined to CD4+CD25+ T Regulatory Cells in Humans", Human Immunology, vol. 66, 2005, pp. 13-20.

Peters, "Ex Vivo Generation of Human Alloantigen-Specific Regulatory T Cells from CD4posCD25high T Cells for Immunotherapy", PLoS One, vol. 3, No. 5, e2233, 2008, pp. 1-13.

Thornton et al., "Expression of Helios, an Ikaros Transcription Factor Family Member, Differentiates Thymic-Derived from Peripherally Induced Foxp3+ T Regulatory Cells", Journal of Immunology, vol. 184, 2010, pp. 3433-3441.

Walker et al., "Induction of FoxP3 and Acquisition of T Regulatory Activity by Stimulated Human CD4+CD25− T Cells", Journal of Clinical Investigation, vol. 112, 2003, pp. 1437-1443.

Wang et al., "Transient Expression of FOXP3 in Human Activated Nonregulatory CD4+ T Cells", European Journal of Immunology, vol. 37, 2007, pp. 129-138.

Wieczorek et al., "Quantitative DNA Methylation Analysis of FOXP3 as a New Method for Counting Regulatory T Cells in Peripheral Blood and Solid Tissue", Cancer Res, vol. 69, 2009, pp. 599-608.

Zand et al., "A Renewable Source of Donor Cells for Repetitive Monitoring of T- and B-cell Alloreactivity", American Journal of Transplantation, vol. 5, 2005, pp. 76-86.

European Office Action received for European Patent Application No. 13754740.2, mailed on Jan. 16, 2017, 3 pages.

\* cited by examiner

_US 9,801,911 B2_

EXPANSION OF ALLOANTIGEN-REACTIVE REGULATORY T CELLS

CROSS-REFERENCE TO RELATED APPLICATIONS

This application is a U.S. National Phase of PCT/US2013/028734, filed Mar. 1, 2013, which claims the benefit of U.S. Provisional Patent Application No. 61/606,329, filed Mar. 2, 2012, each of which is incorporated herein by reference in its entirety.

STATEMENT OF GOVERNMENT SUPPORT

This invention was made with government support under P30 DK063720 awarded by the National Institute of Health. The government has certain rights in the invention.

FIELD

The present disclosure relates generally to the manufacture of regulatory T cells (Tregs) for use in immunotherapy. In particular, the present disclosure relates to robust approaches for the expansion of alloantigen-reactive Tregs ex vivo. Alloantigen-reactive Tregs produced in this way are suitable for the induction and/or maintenance of immunologic tolerance in recipients of allogeneic transplants.

BACKGROUND

Ongoing refinement of immunosuppression regimens has substantially reduced the incidence of acute rejection after solid organ transplantation. However, long-term outcomes have stagnated partly due to morbidity and mortality associated with immunosuppression. The traditional approach to immunosuppression has emphasized non-specific suppression of T cell responses.

The more recent elucidation of T regulatory cells (Tregs) and their importance in regulating immune responses has encouraged the reconfiguration of immunosuppression regimens to favor Treg development and function with the ultimate goal of inducing graft tolerance (Waldmann et al., J. Clin Immunol, 28:716-725, 2008; Kang et al., Am J Transplant, 7:1457-1463, 2007; Walsh et al., J Clin Invest, 114:1398-1403, 2004; Yeung et al., Transplant Proc, 41:S21-26, 2009; Sanchez-Fueyo et al., J Immunol, 176:329-334, 2006; Sagoo et al., Curr Opin Organ Transplant, 13:645-653, 2008; and Long et al., Transplantation, 88:1050-1056, 2009). Multiple preclinical models have shown that adoptive transfer of Tregs can mitigate graft rejection and, in combination with "Treg-supportive" immunsuppression regimens, can induce long-term tolerance (Kang et al., Am J Transplant, 7:1457-1463, 2007; Riley et al., Immunity, 30:656-665, 2009; Issa et al., Expert Rev Clin Immunol, 6:155-169, 2010; and Nadig et al., Nat Med, 16:809-813, 2010). Treg-supportive" immunsuppression regimens have included the initial de-bulking of donor-reactive T cells. Rabbit anti-thymocyte globulin (rATG), a commonly used T-cell depleting agent in transplantation, appears to spare Tregs (Sewgobind et al., Nephrol Dial Transplant, 24:1635-1644, 2009), thereby increasing Treg:T conventional cell (Tconv) ratio. Additionally, sirolimus (SRL) suppresses effector T cells while fostering Treg development (Demirkiran et al., Transplantation, 85:783-789, 2008; and Demirkiran et al., Transplantation, 87:1062-1068, 2009).

Most protocols typically expand all Tregs nondiscriminately to produce cells referred to as polyclonal Tregs (polyTregs). However, alloantigen-specific Tregs (alloTregs) are more effective and safer than non-specific Tregs in transplant settings because they provide specific rather than generic immunosuppression (Golshayan et al., Blood, 109:827-835, 2007; and Raimondi et al., J Immunol, 184:624-636, 2010). In particular, donor-reactive Tregs have the potential to induce tolerance to the transplanted organ without impeding conventional immune responses. Thus what is needed in the art are robust methods for expansion of alloTregs for use in promoting transplant tolerance and for treating graft versus host disease.

SUMMARY

The present disclosure relates generally to the manufacture of regulatory T cells (Tregs) for use in immunotherapy. In particular, the present disclosure relates to robust approaches for the expansion of alloantigen-reactive Tregs (alloTregs) ex vivo. AlloTregs produced in this way are suitable for the induction and/or maintenance of immunologic tolerance in recipients of allogeneic transplants.

The present disclosure provides methods for the production of human, donor-reactive regulatory T cells (Tregs), comprising: a) co-culturing CD19+ B cells of a human donor (first human subject) with irradiated CD40L+ human leukemia feeder cells under conditions effective in producing stimulated B cells (sBc); and b) co-culturing CD4+, CD25+, CD127−/lo T cells of a human recipient (second human subject) with the sBc under conditions effective in selectively expanding human donor-reactive regulatory T cells (Tregs). In some embodiments, the human donor is unrelated to the human recipient. In some embodiments, the human donor is HLA-mismatched in relation to the human recipient (e.g., donor is allogeneic to the recipient or said another way the transplant is a heterologous organ transplant). In some embodiments, the HLA-mismatch comprises a mismatch at one, two, three or four of HLA-A, HLA-B, HLA-C and HLA-DR. In some embodiments, the methods further comprise step c) re-stimulating the donor-reactive Tregs by cross-linking CD3 and CD28 of the donor-reactive Tregs under conditions effective in producing restimulated donor-reactive Tregs. In some preferred embodiments, the donor-reactive Tregs are CD4+, Helios+ and Foxp3+. In some embodiments, the donor-reactive Tregs are CD27+ and CD62L+. In some embodiments, the methods further comprise a step before of a) of isolating CD4+, CD25+, CD127−/lo T cells from cryopreserved peripheral blood mononuclear cells (PBMC) obtained from the human recipient. In some embodiments, step a) comprises co-culturing the B cells and the feeder cells in medium comprising insulin, transferrin, interleukin-4 and cyclosporine A. In some embodiments, the feeder cells are KCD40L cells. In some embodiments, step b) comprises co-culturing the sBc and the CD4+, CD25+, CD127−/lo T cells in medium comprising interleukin-2, after the sBc have been irradiated. In some embodiments, step c) commences 9-12 days after step b) commences. In some preferred embodiments, the re-stimulated alloTregs comprise at least 200, 250, 300, 350, 400, 450, 500, 600, 700, 800, 900, 1000, 1100, 1200, 1400 or 1600 fold more cells than the CD4+, CD25+, CD127−/lo T cells at the onset of step b). Also provided by the present disclosure are compositions comprising a physiologically acceptable buffer (e.g., saline, PBS, etc.) and the restimulated donor-reactive Tregs produced using the methods described above. The present disclosure further provides methods for treating an organ transplant recipient comprising: administering from $10^7$ to $10^{11}$ of the restimulated donor-reactive Tregs produced using the methods described above to a human recipient of a heterologous organ transplant. Also provided are medicaments for treating or preventing rejection of a solid organ allograft by the human recipient, the medicament comprising: from $10^7$ to $10^{11}$ of the restimulated donor-reactive Tregs produced using the methods described above. In some embodiments, the organ transplant is a solid organ allograft selected from the group consisting of cardiac, lung, cardiac/lung, kidney, pancreas, kidney/pancreas, intestine and liver allografts. In some embodiments the solid organ allograft is a skin allograft. In some embodiments, the restimulated donor-reactive Tregs are administered on more than one occasion (repeatedly administered). In some embodiments, the restimulated donor-reactive Tregs are first administered after the recipient has received the heterologous organ transplant. In some embodiments, the restimulated donor-reactive Tregs are administered before and after the recipient has received the heterologous organ transplant. In some preferred embodiments, the methods further comprise subjecting the human recipient to a Treg-supportive immunosuppression regimen before administration of the restimulated donor-reactive Tregs. In some embodiments, the Treg-supportive immunosuppression regimen comprises: administering rabbit antithymocyte globulin to the human recipient at an amount effective to achieve lymphocyte depletion. In some embodiments, the methods further comprise administering prednisone, mycophenolate mofetile and tacrolimus to the human subject at doses below standard of care. In some embodiments, the methods further comprise administering sirolimus to the human subject. In some preferred embodiments, the administration of the restimulated donor-reactive Tregs is effective in reducing the likelihood of acute and/or chronic transplant rejection. In some preferred embodiments, the administration of the restimulated donor-reactive Tregs is effective in prolonging survival of the solid organ allograft. In some preferred embodiments, the administration of the restimulated donor-reactive Tregs is effective in achieving one or more of the following: increasing Treg percentages over baseline, increasing donor-reactive Treg frequency, increasing donor-reactive Treg activity, and induction of tolerance gene expression profiles in PBMC and/or transplant tissue.

As used herein, the singular form "a," "an" and "the" includes plural references unless indicated otherwise.

BRIEF DESCRIPTION OF THE DRAWINGS

9C shows alloreactivity of Tregs expanded with primary allogeneic sBc stimulation and polyclonal restimulation on day 11 determined as described in FIG. 8B. An example of overlay histogram is shown.

DETAILED DESCRIPTION

The present disclosure relates generally to the manufacture of regulatory T cells (Tregs) for use in immunotherapy. In particular, the present disclosure relates to robust approaches for the expansion of alloantigen-specific Tregs ex vivo. Alloantigen-specific Tregs produced in this way are suitable for the induction and/or maintenance of immunologic tolerance in recipients of allogeneic transplants.

Figure 1:
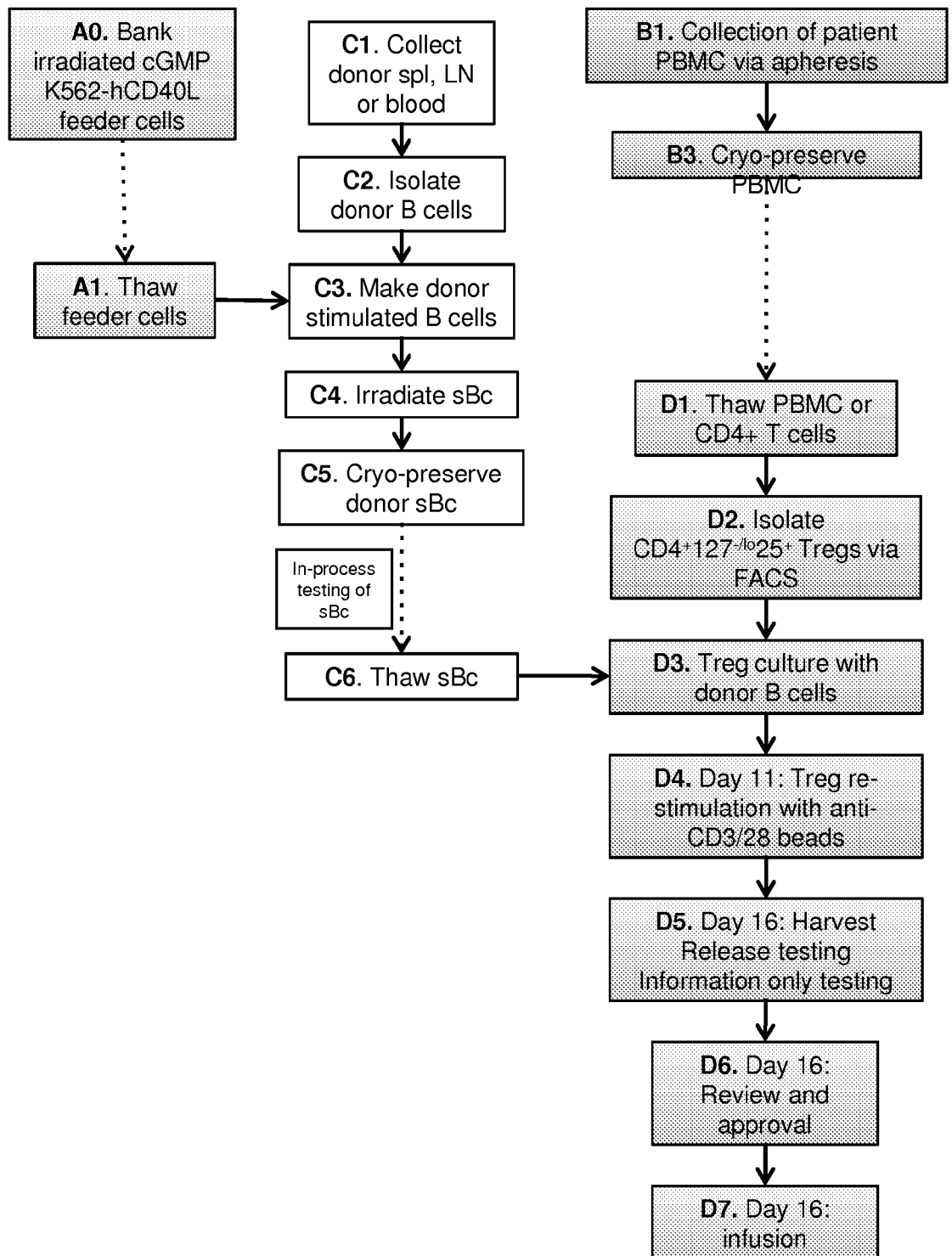
FIG. 1 provides a flow chart of an exemplary donor-reactive regulatory T cell (Treg) manufacturing process.
Figure 2A:
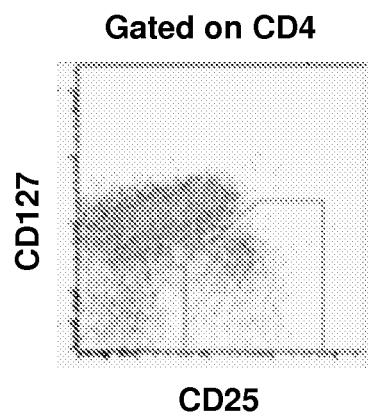
FIG. 2A shows the CD4+CD25+CD127−/lo population of cells purified from recipient PBMC by FACS.

The present disclosure provides methods to selectively expand donor-reactive Tregs 200 to 1,000 fold in less than 20 days. Contrary to the dogma that dendritic cells are most efficient at expanding T cells, CD40 ligand-stimulated human B cells were found to be extremely potent in inducing proliferation of Tregs. FIG. 1 shows the workflow of donor-reactive Treg manufacturing. Briefly, the process begins with stimulating purified donor B cells with lethally irradiated good manufacturing process (GMP)-certified K562-hCD40L transfectants. The stimulated donor B cells are irradiated and used to selectively expand donor-reactive Tregs from CD4+CD25+CD12710 Tregs isolated from recipients' peripheral blood by fluorescent activated cell sorting (FIG. 2A). By day 9 to 12, the Tregs that remained in the culture are virtually all donor-reactive. The Tregs are restimulated with anti-CD3 and anti-CD28-conjugated beads to further expand the cells for additional 5 days. This protocol induces robust proliferation of Tregs (FIG. 2B) and can produce over a billion donor-reactive Tregs from one unit of blood. The expanded Tregs are >95% CD4+, >60% Foxp3+, >90% with demethylated Foxp3 promotor, >90% donor-reactive, and suppress donor-stimulated T cell proliferation when present at a 1:125 Treg:responder PBMC ratio. The donor-reactive Tregs (also referred to herein as alloantigen-specific Tregs or alloTregs) find use in methods for promoting transplant tolerance and for treating graft versus host disease.

An exemplary embodiment involves the use of donor-reactive Tregs in the context of a Treg-supportive immunosuppression regimen as an approach to inducing tolerance of a liver transplant (Ltx). Treg therapy is useful for increasing the likelihood of and/or accelerating the development of tolerance. Because of the exceptionally high frequency of donor-reactive T cells, "debulking" of the host alloreactive repertoire and adjunct immunosuppression are needed to create a more favorable setting for Tregs to control alloimmunity and to ensure long-term graft tolerance (Wells et al., Nat Med, 5:1303-1307, 1999; Li et al., Curr Opin Immunol, 12:522-527, 2000; and Wells et al., Philos Trans R Soc Lond B Biol Sci, 356:617-623, 2001) Importantly, some immunosuppression drugs favor Treg development and/or survival while others are neutral or antagonistic. Thus in some embodiments, Treg administration in organ transplant settings is done in combination with administration of Treg-supportive immunosuppression regimens.

Findings in Treg research in the past 15 years provide a compelling rationale for therapeutic use of donor-reactive Tregs in transplantation. The present disclosure provides the first clinical trial involving the administration of donor-reactive Tregs to solid organ transplant recipients. Development of a good manufacturing practice (GMP)-compliant protocol to reliably expand human donor-reactive Tregs (Example 1) has made this effort possible. Additionally, a set of immune monitoring assays has been developed to dissect alloimmune responses in transplant patients, which have significantly improved sensitivity and reproducibility as compared to previously described assays.

EXAMPLES

The present disclosure is described in further detail in the following examples which are not in any way intended to limit the scope of the disclosure as claimed. The attached figures are meant to be considered as integral parts of the specification and description of the disclosure. The following examples are offered to illustrate, but not to limit the claimed disclosure.

In the experimental disclosure which follows, the following abbreviations apply: M (molar); mM (millimolar); μM (micromolar); nM (nanomolar); mol (moles); mmol (millimoles); μmol (micromoles); nmol (nanomoles); gm (grams); mg (milligrams); μg (micrograms); pg (picograms); L (liters); ml and mL (milliliters); μl and μL (microliters); cm (centimeters); mm (millimeters); μm (micrometers); nm (nanometers); U (units); V (volts); MW (molecular weight); sec (seconds); min(s) (minute/minutes); h(s) and hr(s) (hour/ hours); ° C. (degrees Centigrade); ND (not done); NA (not applicable); rpm (revolutions per minute); H₂O (water); aa (amino acid); by (base pair); kb (kilobase pair); kD (kilodaltons); cDNA (copy or complementary DNA); DNA (deoxyribonucleic acid); ssDNA (single stranded DNA); dsDNA (double stranded DNA); dNTP (deoxyribonucleotide triphosphate); PCR (polymerase chain reaction); qPCR (quantitative PCR); RNA (ribonucleic acid); and RT-PCR (reverse transcription PCR). Additional abbreviations include: Ab (antibody); allo (allogenic); CFSE (carboxyfluorescein diacetate, succinimidyl ester); FACS (fluorescent activated cell sorting); GMP (good manufacturing practice); IHC (immunohistochemistry); Ltx (liver transplant); MELD (model for end-stage liver disease); MLR (mixed lymphocyte reaction); PBMC (peripheral blood mononuclear cells); poly (polyclonal); rATG (rabbit anti-thymocyte globulin); sBcs (stimulated B cells); SOC (standard of care); SRL (sirolimus/rapamycin): tac (tacrolimus); Tconv (conventional T cells); Tregs (regulatory T cells); TSDR (Treg-specific demethylation region); Tx (transplant/transplantation); and UCSF (University of California San Francisco).

Example 1

Production of Donor-Reactive Regulatory T Cells

This example provides an exemplary GMP-compliant method to selectively expand ex vivo up to billions ($10^9$) of alloantigen-specific Tregs from human peripheral blood monocular cells (PBMC) in about 2 weeks (see FIG. 1).

Materials and Methods

Recipient T cell purification and banking. PBMC were purified from whole blood or leukopheresis products from participants using ficoll density centrifugation. The cells were washed twice and resuspended in ice cold CS10 cryopreservation solution (BioLife Solutions) at 100-200 million cells/ml/cryogenic vial. The cells were frozen in a controlled rate freezer and stored in vapor phase of liquid nitrogen until further use.

Donor B cell purification and banking. Donor spleen or lymph nodes from cadaveric donors or PBMC from living donors were collected and transported to the GMP facility for processing into a single cell suspension. B cells were purified using CD19 positive selection on a CliniMACS instrument. Purified CD19⁺ B cells were banked by cryopreservation until needed for Treg expansion.

Feeder cell preparation. Human erythromyeloblastoid leukemia cells, K562 (ATCC No. CCL-243), were transfected with a lentivirus to express human CD40L, CD64 and HLA-DR0401 (K562-hCD40L or K40L). These cells are not tumorigenic in immunodeficient mice. The K40L feeder cells were γ-irradiated at 10,000 rads, and banked until further use.

Banked donor B cell activation. A modified, GMP-compliant protocol (Zand et al., Am J Transplant, 5:76-86, 2005) was used to generate stimulated B cells (sBc). Specifically, ~1-100×10⁶ donor B cells purified with paramagnetic anti-CD19 microbeads on a CliniMACS (Miltenyi) were stimulated with banked, GMP-compliant, γ-irradiated K40L cells at a 1-2:1 ratio (B:K40L) for 7 days in a medium containing 10% human AB serum, insulin, transferrin, human recombinant IL-4, and cyclosporine A. On day 7, the mixed culture was restimulated with K40L feeder cells at a 1-10:1 ratio (B:K40L) for 3 days. The average expansion was 10 to 20 fold. The sBc were passed over ficoll to remove dead cells including the dead K40L cells. A set of quality assurance assays were performed on the sBc, which included a qPCR-based EBV reactivation test (Viracor) and flow cytometry to determine purity as well as expression of HLA-DR, CD80, and CD86. The sBc were γ-irradiated (1000 rads) and banked until further use.

Treg expansion. Recipient PBMC were thawed, counted and stained with clinical-grade, fluorescently-conjugated antibodies (CD4-PerCP Ab, CD25-APC Ab, and CD127-PE Ab). CD4⁺CD127$^{lo/-}$CD25⁺ cells were purified from the stained PBMC by FACS (FIG. 2A). FACS-purified Tregs were mixed with banked irradiated sBc at a 4:1 ratio of sBc:Treg in growth medium comprising GMP-grade Optimizer Medium (Invitrogen) containing supplement, GlutaMAX-1 CTS and 2% human AB serum. On day 2, human recombinant IL-2 was added to the culture at a total concentration of 300 IU/ml when media volume was doubled. The cultures were fed with fresh medium containing IL-2 on days 5, 7 and 9 to maintain cell concentration at $2-3\times10^5$ cells/ml. On day 11 of the culture, cells were restimulated with beads conjugated with anti-CD3 and anti-CD28 monoclonal antibodies at a 1:1 ratio for the remainder of the culture period. The cultures were fed on day 1 and harvested on day 16. The Tregs expand 200 to 1600 fold in the 16-day culture period.

Tregs are resuspended in HypoThermosal solution and kept at 4° C. while awaiting the results of release assays, quality assurance review and approval. Upon product release, the Tregs are transported to the clinic for infusion. Greater than $5\times10^6$ Tregs are purified from one unit of recipient whole blood. With a conservative estimate of 200-fold expansion, at least $1\times10^9$ donor-reactive Tregs are expected to be harvested at the end of the expansion period.

Release assays and release criteria. The following assays and criteria are used before Treg release: viability>99%, flow cytometry for CD4>90%, CD8<5%, CD19<5%, Foxp3>60%, and TSDR>80%. Negative microbial tests for bacteria, fungus, mycoplasma, and endotoxin on culture day 12. The TSDR assay employed is currently the most accurate and reliable test for the purity and stability of Tregs. The methylation assay confirms the percentage of Foxp3+ cells determined by flow cytometry. Additionally, there is strong evidence that Foxp3 can be expressed in activated Tconv cells. However, the Foxp3 TSDR locus is methylated in activated Tconv cells while it is demethylated in bona fide Tregs.

Post-release assays. The following assays are performed on each product to fully document the phenotype and functionality of the cells: 1) expanded flow cytometric analysis using two panels consisting of CD4/Foxp3/CD27/CD62L and CD4/Foxp3/CD25/Helios; 2) donor specific suppression assay; 3) donor specificity assay; 4) long-term 14-day microbial test; and 5) cytokines (IL-2, IFN-gamma and IL-17) induced by donor sBc and PMA and ionomycin.

Recent experimental evidence suggests that Foxp3+ Tregs are "plastic" and can acquire expression of effector cytokines such as IFN-gamma and IL-17 (Zhou et al., Curr Opin Immunol, 21:281-285, 2009; Zhou et al., Immunity, 30:646-655, 2009; and Hori et al., Curr Opin Immunol, 22:575-582, 2010). It is helpful to distinguish two types of plastic Treg fates, one that results in loss of Foxp3 expression and concomitant effector cytokine expression (exTregs) (Komatus et al., Proc Natl Acad Sci USA 106:1903-1908, 2009; Xu et al., J Immunol, 178:6725-6729, 2007; Osorio et al., Eur J Immunol, 38:3274-3281, 2008; Yang et al., Immunity, 29:44-56, 2008; and Zhou et al., Nat Immunol, 10:1000-1007, 2009) and the other one that leads to co-expression of Foxp3 and effector cytokines (effector Tregs) (Tartar et al., J Immunol, 184:3377-3385, 2010; Beriou et al., Blood, 113:4240-4249, 2009; Radhakrishnan et al., J Immunol, 181:3137-3147, 2008; Oldenhove et al., Immunity, 31:772-786, 2009; Stroopinsky et al., Eur J Immunol, 39:2703-2715, 2009; Koch et al., Nat Immunol, 10:595-602, 2009; and Hvhannisyan et al., Gastroenterology, 140:957-965, 2011). While exTregs have low or no suppressive activity and can be pathogenic in experimental autoimmune settings, it is important to note that emergence of exTreg in lymphoreplete hosts primarily occurs in extreme experimental conditions (Rubtsov et al., Science, 329:1667-1671, 2010). Moreover, in all conditions, the majority of exTregs do not express effector cytokines even after supraphysiologic in vitro stimulation with PMA and ionomycin. The donor-reactive Tregs produced using the exemplary protocol we have high levels of Foxp3, TSDR, and Helios expression. These cells are infused into patients under Treg-supportive immunosuppression, therefore the chance of the infused donor-reactive Tregs turning into full-fledged pathogenic effectors in vivo is low. In contrast to exTregs, effector Tregs have been shown to be suppressive in many experimental conditions. In particular, IFN-gamma production by Tregs has been shown to be essential to their suppressive function and protection against allograft rejection (Sawitzki et al., J Exp Med, 201:1925-1935, 2005). Thus, effector cytokine production by Foxp3+ Tregs is expected to be tolerogenic rather than pathogenic. The infusion of donor-reactive Tregs that have high, stable Foxp3 expression based on TSDR assay into patients undergoing Treg-supportive immunosuppression is expected to prevent the potential conversion of the donor-reactive Tregs into pathogenic exTregs.

Results

Expansion of donor-reactive Tregs. The methods described above using CD40L-stimulated donor B cells (sBc) as antigen presenting cells (APC) are suitable for the selective expansion of donor-reactive regulatory T cells starting with FACS purified CD4$^+$CD127$^{lo/-}$ CD25$^+$Tregs from recipient PBMC. Extensive testing showed that virtually all the live cells that remain in the culture 8 to 10 days after stimulation are donor reactive. The cells were then further expanded by polyclonal restimulation using anti-CD3 and anti-CD28 conjugated beads. Tregs were purified from PBMCs using FACS based on CD4$^+$CD127$^{lo/-}$CD25$^+$ cell surface phenotype as previously described (Putman et al., Diabetes, 58:652-662, 2009). Donor B cells were purified using anti-CD19 CliniMACS beads (Miltenyi) and stimulated with irradiated GMP-compliant K562 cells expressing human CD40L. The dead K540L cells were removed from the sBc by ficoll density gradient centrifugation and the purified sBc were irradiated before adding to purified Tregs. Using this protocol, up to ~1600-fold expansion of Tregs was achieved. Given that 10% of Tregs are reactive to a fully HLA-mistmatched donor, 1600-fold overall expansion translates into ≥16,000-fold increase in donor-reactive Tregs in the 16-day culture period.

Figure 2B:
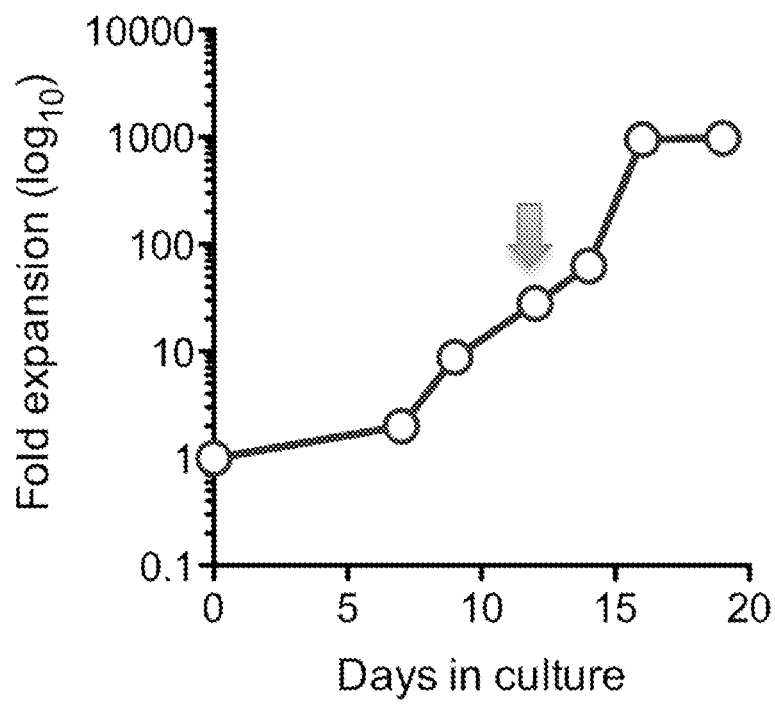
FIG. 2B shows the magnitude of expansion of donor-reactive Tregs achievable with the methods of the present disclosure. The arrow indicates when the Tregs were exposed to polyclonal stimulus (e.g., anti-CD3/CD28 conjugated beads).
Figure 3:
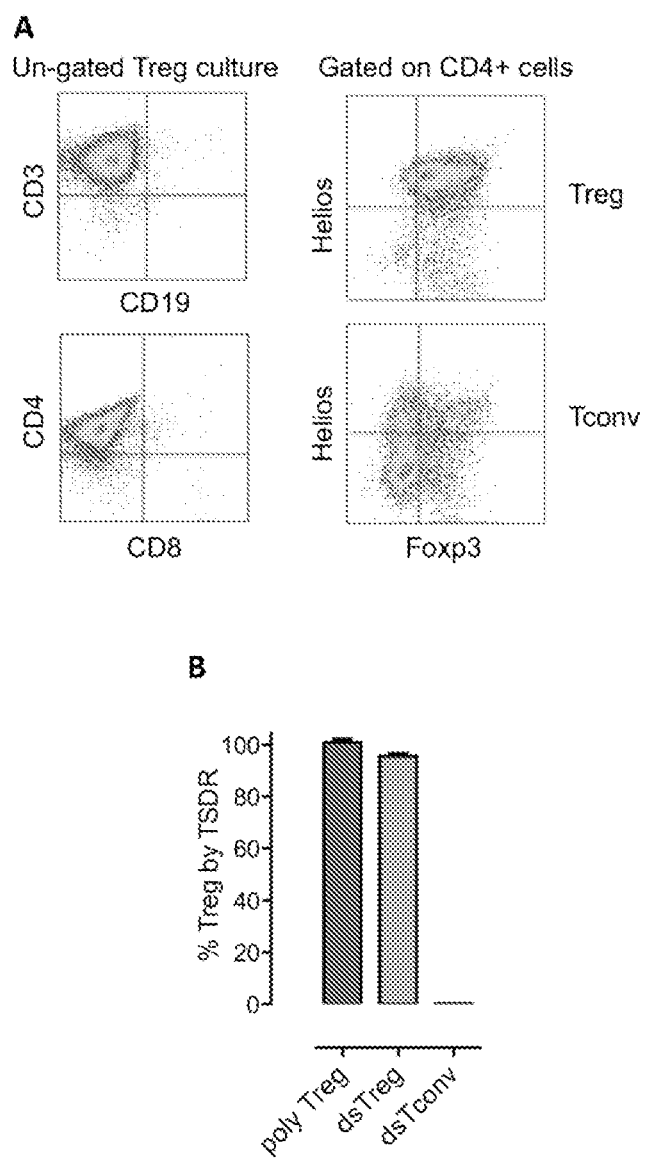
FIG. 3A is a flow cytometric analysis of the expanded donor-reactive Tregs and control donor-reactive T conventional cells (Tconv).
FIG. 3B shows Treg-specific demethylated region (TSDR) analysis of expanded donor-reactive Tregs and Tconv and polyclonal Tregs (polyTregs) expanded using a polyclonal stimulus (anti-CD3/anti-CD28 coated beads).
Figure 4A:
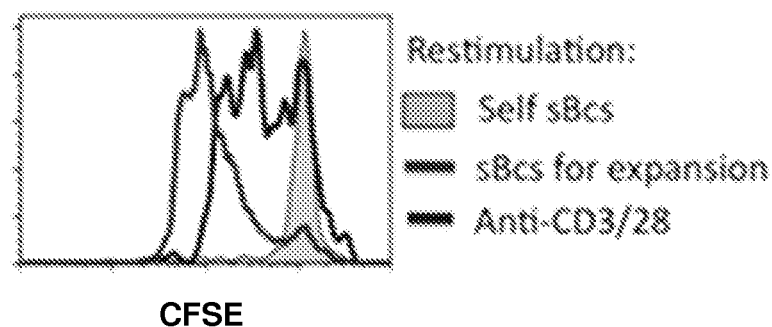
FIG. 4A provides results of a donor specificity assay. Donor-reactive Tregs were labeled with CFSE and restimulated as indicated.
Figure 4B:
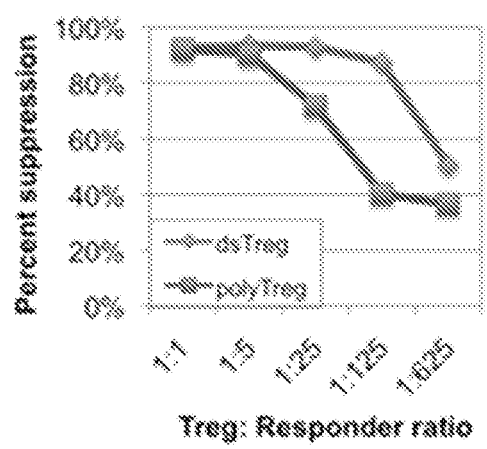
FIG. 4B provides results of a mixed lymphocyte reaction (MLR) suppression assay. Titrated number of donor-reactive Treg and polyclonally expanded Tregs were mixed with 2.5×10$^4$ autologous PBMC and 1.25×10$^5$ irradiated donor PBMC and incubated for 6 days. Tritiated-thymidine was added during the last 16 hours. Suppression of thymidine incorporation was calculated by comparing counts per minute (CPM) in wells without Tregs.
Figure 5:
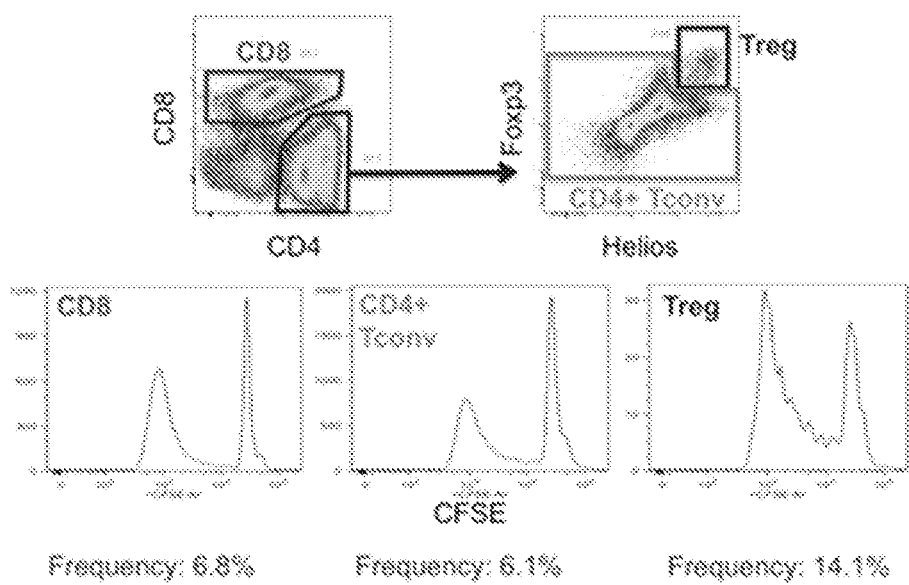
FIG. 5 shows results of a donor-reactive T cell frequency assay. Recipient PBMC were labeled with CFSE and stimulated with donor sBc for 3.5 days. The culture was harvested, stained for CD3, CD4, CD8, Foxp3 and Helios, and analyzed on a flow cytometer. The CFSE probiles of CD8, CD4+ Tconv, and Tregs were used to calculate the frequencies of donor-reactive T cells in each subset.

A series of protocols were established to assess the phenotype and functional capacities of the expanded donor-reactive Tregs. The expanded Treg cultures were CD3+ CD4+CD8−CD19−, Foxp3+, Helios+, CD27+ and CD62Lhi when compared to similarly expanded Tconv cells (FIG. 2B). Almost all donor sBc-expanded Tregs responded to restimulation with the donor sBc, but not to syngeneic sBc, indicating that they are stimulator-reactive (FIG. 4A). The donor-sBc-expanded Tregs exhibited enhanced donor-specific suppressive activity when compared with polyclonally expanded Tregs (FIG. 4B). An important issue is whether the donor-reactive Treg were stable Tregs or T effector cells that may have transiently upregulated Foxp3. Demethylation of the Foxp3 promoter has been shown to be a robust marker for stable Foxp3 expressing Treg (Wang et al., Eur J Immunol, 37:129-138, 2007; and McClymont et al., J Immunol, 186:3918-3926, 2010). Greater than 94% of the donor-reactive Tregs, and less than 1% of dsTconv, have demethylated Foxp3 promoter (FIG. 3B) as determined by a quantitative Treg-Specific Demethylation Region (TSDR) assay (Wieczorek et al., Cancer Res, 69:599-608, 2009). Together, these results demonstrate that the exemplary protocol reliably expands GMP-grade donor-reactive Tregs. Release assay results from a typical expansion are shown in FIG. 5.

Example 2

Liver Transplantation Using Donor-reactive Tregs and Treg-Supportive Immunosuppression This example describes a dose escalation clinical trial to assess safety of autologous, donor-reactive Treg therapy in liver transplant (Ltx) recipients. However, the methods and compositions of the present disclosure are not limited to this context. In fact, the methods and compositions of the present disclosure are expected to find use in the context of other solid organ allografts, as well as in treating or preventing graft versus host disease. Donor-reactive Tregs and Treg-supportive immunosuppression are expected to be suitable for inducing or maintaining tolerance of allografts selected from but not limited to cardiac, lung, cardia/lung, kidney, pancreas, kidney/pancreas, intestine and liver allografts.

Escalating doses of Tregs expanded ex vivo using activated donor B cells are administered to Ltx recipients in conjunction with a modified immunosuppression regimen designed to favor Treg development, persistence, and function. This regimen is comprised of rabbit anti-thymocyte globulin (rATG) induction, reduced dosing of corticosteroids (Pred), mycophenolate mofetil (MMF), and tacrolimus (tac), followed by the delayed introduction of sirolimus (SRL). Subjects are followed for one year after transplantation, during which clinical data along with peripheral blood (PBMC and serum) and liver biopsy samples are collected and analyzed.

Primary Objectives. The following outcomes are assessed for adult, de novo Ltx recipients: one year acute rejection rate ("Banff schema for grading liver allograft rejection: an international consensus document," Hepatology, 25:658-663, 1997); one year chronic rejection rate ("Liver biopsy interpretation for causes of late liver allograft dysfunction,", Hepatology, 44:489-501, 2006); rate of ≥grade 3 infection three months after Treg infusion; rate of ≥grade 3 wound complications; rate of ≥grade 3 anemia, neutropenia, and/or thrombocytopenia.

Secondary Objectives. The following outcomes are also assessed: increase of Treg percentages over baseline; increase of donor-reactive Treg frequency; increase of donor-reactive Treg activity; and detection of tolerance gene expression profiles in PBMC and/or liver tissue.

Patient population and inclusion/exclusion criteria. The clinical trial encompasses three phases with specific inclusion/exclusion criteria at each phase to maximize participant safety.

Pre and Ltx phase. Patients are selected from the Ltx waiting list who have end-stage liver disease, between the ages of 20-70 years, and have a calculated MELD score of no greater than 25 (Kamath et al., Hepatology, 33:464-470, 2001). The trial specifically excludes Ltx recipients at increased risk of acute rejection and recurrent disease and limits the severity of liver disease and portal hypertension and/or hypersplenism. In some embodiment, only patients with Tregs present in PBMC at greater than 10/µl are selected.

Eligible patients undergo leukopheresis to isolate PBMC, which are cryopreserved for subsequent Treg purification and expansion. At the time of tx and after verification of the participant's ongoing eligibility, donor spleen and or lymph nodes along with liver biopsy tissue are collected and banked.

Treg-supportive immunosuppression phase. Ltx recipients must be out of the ICU and initiate rATG induction no later than post-tx day 3. They receive a total dose of 3-4.5 mg/kg rATG to achieve lymphocyte depletion, defined as CD3 count <50/mm3. This dose range was chosen to achieve adequate debulking (Wong et al., Transpl Int, 19:629-635, 2006) while minimizing immunosuppression. The timing and setting of rATG administration was chosen to avoid the potential for over-immunosuppression and/or cytokine release syndrome/hematologic toxicities in medically unstable recipients. Patients are assessed for eligibility to convert to sirolimus (SRL)-based immunosuppression and must have normal allograft function, as well as adequate renal function, hematologic parameters, wound healing, and hepatic artery patency between 4-6 weeks after Ltx.

The immunosuppression regimen for study subjects was specifically designed to foster Treg development while optimizing participant safety. Study participants start on standard of care (SOC) immunosuppression with half-dose corticosteroids and half-dose mycophenolate mofetile (MMF). Tacrolimus (Tac) is initiated, targeting reduced levels of 6-8 µg/L compared to SOC (10-15 µ/L). No later than post-tx day 3, patients receive a course or rATG (3.0-4.5 mg/kg total dose) to deplete lymphocytes (CD3 count <50/mm$^3$ or when the maximal dose has been given). Participants who are off corticosteroids convert to SRL-based immunosuppression between 4-6 weeks after tx with SRL initiation to target levels of 6-8 µg/L, and reduction of tag to trough levels of 3-5 µg/L. MMF is discontinued. Four weeks after conversion to SRL-based IS (8-10 weeks after tx), participants undergo final assessment, including allograft biopsy to ensure eligibility to receive Treg infusion. Six months after tx, SRL is further reduced to target levels of 4-6 µg/L.

TABLE 2-1

Immunosuppression (IS) Plan For Liver Transplant Patients

| Day or Week | Transplant Hospitalization LTx/Treg-supportive IS | | | | Out-patient Follow-up Sirolimus conversion | |
|---|---|---|---|---|---|---|
| | D 0 | D 3 | D 5 | D/C | Wk 5-10 | Wk 11-12 |
| Pred (mg/d) | 500 | → | → | 20 | 0 | 0 |
| MMF (mg/d) | 1000 | → | → | 1000 | → → → 0 | 0 |
| Tac (µg/L) | 0 | 6-8 | 6-8 | 6-8 | → 3-5 | 3-5 |
| rATG (mg/kg) | 0 | 3.0-4.5 | 3.0-4.5 | 3.0-4.5 | 0 | 0 |
| SRL (µg/L) | 0 | 0 | 0 | 0 | → 6-8 | 6-8 |
| dsTregs | 0 | 0 | 0 | 0 | 0 | Infusion |

Treg infusion phase: Approximately 10-12 weeks after Ltx, participants are assessed for suitability to receive donor-reactive Tregs. Data regarding the kinetics of T cell recovery after rATG show stable T cell numbers between 4-12 weeks after tx. Therefore, the Treg infusion at 10-11 weeks after tx is in the setting of a debulked immune system. Participants must have normal allograft function in the context of stable SRL-based immunosuppression.

In parallel with the immunosuppression conversion, donor B cells are expanded for 10 days and then used to expand Tregs over an additional 16 days (Example 1). Expanded donor-reactive Tregs passing all release criteria are available for infusion between 10-11 weeks after tx.

After Treg infusion, blood is collected on days 1, 3, 7, and 28 for mechanistic studies. Clinical laboratory assessments continue weekly for 4 additional weeks. If liver tests remain stable, clinical laboratory assessments revert to the SOC for the remainder of study. Additional blood is drawn at 1 year after Ltx for mechanistic studies and an additional protocol liver biopsy is performed 1 year after Ltx for detailed histological and immunohistochemical analyses.

Dose escalation plan: Eligible patients receive either no Treg infusion or a single infusion of donor-reactive Tregs at 3 dose levels: 50, 200, and 800 million. Progression from one group to the next is based on the occurrence of dose-limiting toxicity.

TABLE 2-2

Comparison To Current Standard Of Care

| | rATG + SRL | | | | Standard of Care | | | |
|---|---|---|---|---|---|---|---|---|
| Week | Wk 1 | Wk 5 | Wk 13 | Wk 24 | Wk 1 | Wk 5 | Wk 13 | Wk 24 |
| Pred (mg/d) | 500 → 20 | 0 | 0 | 0 | 1000 → 20 | 7.5 | 5.0 | 5.0 |

TABLE 2-2-continued

Comparison To Current Standard Of Care

| Week | rATG + SRL | | | | Standard of Care | | | |
|---|---|---|---|---|---|---|---|---|
| | Wk 1 | Wk 5 | Wk 13 | Wk 24 | Wk 1 | Wk 5 | Wk 13 | Wk 24 |
| MMF (mg/d) | 1000 | 1000 → 0 | 0 | 0 | 2000-3000 | 2000 | 1500 | 1000 |
| Tac (µg/L) | 6-8 | 6-8 → 3-5 | 3-5 | 3-5 | 10-12 | 10-12 | 8-10 | 6-8 |
| rATG (mg/kg) | 3.0-4.5 | 0 | 0 | 0 | 0 | 0 | 0 | 0 |
| SRL (µg/L) | 0 | 0 → 6-8 | 6-8 | 4-6 | 0 | 0 | 0 | 0 |

Example 3

Immunologic Analyses

This example describes analyses that are done on peripheral blood and liver tissues to assess the effects of Treg-supportive immunosupression and Treg therapy on alloimmune responses. donor-reactive Treg therapy along with Treg-supportive immunosuppression is expected to have a measurable impact on the frequency of donor-reactive Treg and on anti-donor T cell responsiveness. Additionally, the exemplary therapeutic regimen described in Example 2 is expected to lead to an earlier development of an immune tolerance signature than occurs with conventional (SOC) immunosuppression regimens. Analyses include one or more of the following: 1) T cell functional and phenotypic analyses; 2) tolerance gene expression signature in PBMCs and protocol biopsy samples; and 3) histological analyses of for-cause as well as protocol biopsy samples.

T cell phenotype and function analyses. Multiparameter flow cytometry (MFC) is used to profile leukocyte subpopulations, determine frequencies of donor-reactive T cells, assess donor-specific suppression by Tregs, and profile donor-antigen induced gene and cytokine expression. Together, these assays permit the assessment of the contribution of four known mechanisms of immune tolerance—deletion, deviation, anergy/exhaustion, and regulation.

Frequency of donor-reactive T cells. This assay is used to determine the frequency of donor-reactive CD4+ Tconv cells, CD8+ T cells, and Tregs. Banked PBMC samples are compared from pre-transplant/transplant, pre-Treg/post SRL conversion, on days 1, 3, 7, and 28 after Treg infusion, and at one year post transplant. An increase in donor-reactive Treg shortly after infusion is expected, especially in the cohorts receiving 200-800×10$^6$ dsRegs.

In vitro suppression assay. This assay is used to evaluate suppression by Tregs isolated from pre-transplant, pre-Treg infusion/post SRL conversion, at days 1 and 28 after Treg infusion, and 1 yr after liver transplant time points. Pre-transplant leukophoresed PBMC are used as responders mixed with Tregs isolated from various time points. The cultures are stimulated with irradiated donor PMBC to assess donor-specific suppression or with anti-CD3 and anti-CD28 to assess non-specific suppression.

Multiparameter flow cytometry (MFC). MFC is used to determine the percentage of leukocyte subsets in peripheral blood using panels of antibodies developed in our lab. Samples collected from panels and markers used are summarized in Table 3-1.

TABLE 3-1

Multiparameter Flow Cytometry Panels and Marks.

| Panel | Cell # | Markers | | | | | | |
|---|---|---|---|---|---|---|---|---|
| Leukocyte Subsets | 0.25 m | CD45 | CD14 | CD3 | CD19 | CD56 | CD16 | CD4 CD8 |
| Effector/Memory/Naïve T cells | 0.5 m | CD3 | CD4 | CD8 | CD45RA | CD27 | CD28 | CD38 HLA-DR |
| Tregs | 1 m | CD3 | CD4 | CD25 | CD127 | Foxp3 | Helios | |
| Cytotoxicity | 1 m | CD3 | CD19 | CD4 | CD8 | CD56 | CD16 | Perforin GzB |
| TCR | 1 m | CD3 | TCRab | CD19 | Vd1 | Vd2 | | |
| B cells | 0.5 m | CD3 | CD19 | CD20 | CD27 | CD38 | | |

T cell activation/differentiation assay. CD4+ Tconv cells and CD8+ T cells from pre-transplant, pre-Treg/post SRL conversion, on days 1, 3, 7, and 28 after Treg infusion and 1 yr post transplant are stimulated using donor sBc for 3.5 days. The sample collected at pre-transplant, pre-Treg/post SRL conversion, on days 1, 3, 7, and 28 after Treg infusion time points is analyzed for cytokine gene expression using qPCR arrays and cytokine secretion into the supernatant using a 42-plex Luminex assay. The samples collected at pre-transplant and 1 yr after transplant are used to analyze gene expression profiles using gene array and the cytokine in the supernatant is analyzed using a 42-plex Luminex assay. Using qPCR assays, changes in donor-sBc stimulated gene expression are expected to be observed in liver transplant patients. This assay permits alternations in donor-antigen stimulated gene expression profiles to be determined.

Gene expression analyses. Peripheral blood samples are analyzed using microarrays with a previously identified narrow subset of genes representing the most promising biomarkers currently available to detect operational tolerance after liver transplant (Martinez-Llordella et al., J Clin Invest, 118:2845-2867, 2008).

Histological analyses and multiplex immunohistochemistry (mIHC). Extensive histology and mIHC analysis of protocol biopsy samples obtained pre-transplant and at 1 year after liver transplant is performed. Histological analyses evaluate 40 histopathological features to determine tissue integrity and degree of inflammation as shown in Table 3-2.

TABLE 3-2

Multiplex Immunohistochemistry Markers

| mIHC panel | Rationale |
|---|---|
| C4d/CD31 | Decrease in C4d deposits on the hepatic microvasculature is associated with Ltx tolerance. Determine if Treg therapy leads to decrease in C4d deposits |
| CD3/γδ-1/γδ-2 | Portal tract ratio of γδ-1/γδ-2 >1.0 is associated with operational tolerance. Determine if Treg therapy promote this signature |
| CD3/CD45RO/ CD45RA | Monitor the relative ratio of naive to memory T cells; test whether Treg therapy leads to a reduction in portal-based CD3+/CD45RO+ (memory) T cells |
| CD4/Tbet/GATA-3/IL-17/FoxP3 | Monitor the polarization of CD4+ lymphocytes within the allograft to determine whether an increase of putative regulatory T cells contributes to tolerance. |
| IL10/TGFβ/ HLADR | Monitor expression of immunomodulatory cytokines by HLA-DR expressing cells in the liver such as Kupffer's cells and B cells. |
| CK19/CD31/ HLADR | Up-regulation of HLA-DR on biliary epithelium (CK19+) and vascular endothelium (CD31+) makes these cells targets of immune rejection. Determine if Treg therapy prevents DR induction. |

Example 4

Clinical Grade Manufacturing and Therapeutic Advantage of Alloantigen-Reactive Human Regulatory T Cells in Transplantation This example demonstrates a manufacturing process that can generate billions of human alloantigen-reactive regulatory T cells (Tregs) in short-term cultures using GMP-compliant reagents. The process uses CD40L-activated allogeneic B cells to selectively expand alloantigen-reactive Tregs followed by polyclonal restimulation to increase yield. Tregs expanded 200 to 1600 fold, were highly alloantigen reactive, and expressed the phenotype of stable Tregs. The alloantigen-expanded Tregs were 5 to 25 times more potent than polyclonally expanded Tregs in vitro and were more effective at controlling allograft injuries in vivo in a humanized mouse model of skin transplantation.

Materials and Methods

Cell sources. Normal donors were recruited and consented for whole blood donation. When large numbers of cells were required, de-identified apheresis products from normal donors were obtained from the UCSF Blood Center. PBMC were isolated using a Ficoll-Paque PLUS density gradient (GE Healthcare Bio-Sciences AB, Pittsburgh, Pa.) and used fresh or after cryopreservation in CryoStor CS10 freezing medium (BioLife Solutions, Bothell, Wash.) using CoolCell™® devices (BioCision, Mill Valley, Calif.). Spleens were obtained from cadaveric organ donors with research consent. All procedures were approved by the Committee on Human Research at University of California San Francisco and Guy's hospital at King's College London.

Generation of CD40L expressing feeder cells. Lentiviral vectors encoding human CD40L (NM_000074), CD64 (BC032634), DRA (BC071659) and DRB 0401[33] were produced as previously described[34]. These vectors were used to transduce K562 cells to generate a KT64-CD40L.HLADR0401 cell line and FACS was used to generate single cell clones as previously described[35]. Stable expression of expanded clones was verified by flow cytometry using antibodies to CD40L, HLA-DR, and CD64 from BD Biosciences, San Jose, Calif.

Generation of CD40L-sBc. B cells were enriched from PBMC or spleen using the untouched human B cells enrichment kit (Invitrogen, Carlsbad, Calif.). Enriched B cells were cultured with irradiated (40Gy) 3T3 or K562 cells expressing human CD40L as described before[36]. For some experiments, dissociated splenocytes was cultured with CD40L-expressing cells without prior enrichment of B cells. The CD40L-sBc were irradiated (30Gy) and used to stimulate Tregs or cryopreserved in CryoStor CS10 freezing medium until use. For GMP-compliant expansions, peripheral blood B cells were purified using CD19 positive selection on a CliniMACS (Miltenyi Biotech, Germany), stimulated with irradiated (100Gy) K-CD40L cells in transferrin-containing X-VIVO15 medium (Lonza, Walkersville, Md.) supplemented with 10% human AB serum (Valley Biomedical, Winchester, Pa.), GMP grade IL-4 (Miltenyi), and Cyclosporine A (Teva Pharmaceuticals, North Wales, Pa.).

MLR. Responder PBMC labeled with 1.25 μM CFSE (Invitrogen) were stimulated with irradiated allogeneic CD40L-sBc (two sBcs per PBMC) or with irradiated allogeneic PBMCs (5 stimulators per responder). The cultures were harvested after 84 to 96 hrs, stained with anti-CD3 PerCP (BD), anti-CD4 PE-Cy7 (BD), anti-CD8 APC-Cy7 (BioLegend, San Diego, Calif.), efluor 506 fixable viability dye (eBioscience, San Diego, Calif.). The cells were then fixed and permeabilized using a FOXP3 Fixation/Permeabilization buffer set (eBioscience) before staining with anti-FOXP3-Alexa Fluor 647 (eBioscience) and anti-HELIOS PE (BioLegend). Flow cytometry was performed on Fortessa (BD), and analysis was done using FACSdiva (BD) or FlowJo software (Treestar, Ashland, Oreg.).

Treg expansion. Tregs were isolated using a BD FACSAria II (BD) based on the cell surface phenotype of $CD4^+CD127^{lo/-}CD25^+$ and polyclonal expansions of Tregs were performed as previously described[28]. The clinically compliant sorting utilized cGMP mAbs generated and kindly provided by Noel Warner (BD). For alloantigen-reactive Treg expansions, the cultures were maintained in OpTmizer T Cell Expansion Medium (Invitrogen) supplemented with 1% GlutaMAX (Invitrogen), Penicillin/Streptomycin, and 2% human AB serum or X-VIVO15 medium supplemented with 10% human AB serum. FACS purified Tregs were mixed with CD40L-sBc at a 4:1 sBc to Treg ratio. The cultures were maintained with medium containing 300 IU/ml human IL-2 until day 9 or 11, when the cells were restimulated with new irradiated sBc at 4 sBc per Treg ratio or with anti-CD3/anti-CD28-coated beads at a 1:1 bead to cell ratio. Cultures were fed 3 days later and harvested on day 5 after restimulation.

Flow cytometry. Phenotype of expanded Tregs was assessed using three flow cytometric panels. The first panel consisted of anti-CD8 FITC, anti-CD4 PerCP, anti-CD3 PE, and anti-CD19APC. The second panel consisted of anti-CD4 PerCP, anti-CD62L PE, anti-CD27 APC, and anti-FOXP3 Alexa Fluor 488 (BioLegend, Clone 206D). The third panel consisted of anti-CD4 PerCP, anti-CD25 APC, anti-HELIOS PE (BioLegend), and anti-FOXP3 Alexa Fluor 488. Mouse IgG1 Alex Fluor 488 and mouse IgG1 PE (BioLegend) were used to control for FOXP3 and HELIOS staining, respectively. The stained cells were analyzed on a FACSCalibur and the data was analyzed using FlowJo. The CD40L-sBc were analyzed on an AccuriC6 (BD) flow cytometer after staining with anti-HLA-DR PE, anti-CD80 FITC, anti-CD86 PerCP-Cy5.5, and anti-CD19 APC. The data were analyzed using Cflow PLUS software (BD). All antibodies were from BD Biosciences unless otherwise noted.

Treg specificity assay. Expanded Tregs were labeled with 1.25 µM CFSE and stimulated with allogeneic or autologous CD40L-sBc, anti-CD3 and anti-CD28-coated beads, or left unstimulated in media containing 30IU/ml IL-2. After 72 hours, the cells were collected and stained with anti-CD4 APC (BD) and propidium iodide and analyzed on an AccuriC6 flow cytometer.

In vitro suppression assays. Titrated numbers of expanded Tregs were mixed with $3 \times 10^4$ PBMCs from the Treg donor in V-bottom 96 well plates in triplicates. The cells were stimulated with irradiated PBMCs from the sBc donor for 7 days and incorporation of $^3$[H] thymidine during the final 16-20 hours of culture was used to measure proliferation. Cultures containing no expanded Tregs were used as controls. Percent suppression was calculated as: [1−(mean cpm PBMC with Tregs/mean cpm PBMC without Tregs)]×100.

TSDR methylation assay. Genomic DNA isolated from $0.5 \times 10^6$ expanded Tregs using licensed reagents from Epiontis GmbH (Berlin, Germany) according to protocol established by Epiontis GmbH[37]. The assay was performed in triplicated and the percentages of methylated TSDR were calculated as: [mean copy numbers of unmethylated DNA/(mean copy numbers of unmethylated+mean copy numbers of methylated DNA)]×100. For cultures expanded using female donors, the percentages from the above calculation were multiplied by 2 to correct for X chromosome inactivation.

In vivo assessment of Treg function in humanized mouse model of skin transplant. BALB/c.Rag2$^{-/-}$γc$^{-/-}$ mice (Charles River) were bred and maintained in the Biological Services Unit of King's College London under specific-pathogen-free conditions. De-identified human skin was obtained from patients who had undergone routine abdominoplasty and reduction mammaplasty with informed consent and ethical approval. The skin was transplanted onto 8-12 week old BALB/c.Rag2$^{-/-}$γc$^{-/-}$ mice and allowed to engraft for 6 weeks before injection of $10 \times 10^6$ HLA mismatched CD25-depleted human PBMC. Some mice were co-injected with $2 \times 10^6$ ex vivo expanded polyclonal or alloantigen-reactive Tregs. Visual and tactile inspections of the grafts were performed two times weekly. Histological analysis of the grafts was performed 6 weeks after PBMC injections. For the total duration of these experiments, 100 µg purified anti-mouse Gr1 mAB (Bio X Cell, West Lebanon, N.H.) was injected intraperitoneally every 4-5 days to deplete mouse granulocytes. All procedures were conducted in accordance with institutional guidelines and the Home Office Animals Scientific Procedures Act (1986). Frozen sections (6 to 8 µm) of human skin grafts were fixed with 5% paraformaldehyde and stained with antibodies against human antigens ki67 (clone 4A1, Abcam, Cambridge, Mass.), CD45 (clone HI30, eBioscience), CD3 (A0452, Dako, Denmark), FOXP3 (clone 259D/C7, eBioscience), involucrin (clone SYS, Sigma) and CD31 (ab28364, Abcam), followed by incubation with appropriate fluorochrome-conjugated secondary antibodies and mounted with Prolong Gold Anti-fade Reagent with 4-6-diamidino-2-phenylindole (DAPI) (Invitrogen). Samples were subjected to quantitative analysis using fluorescence microscopy by counting four to six non-overlapping visual fields. The individual reading the slides was blinded to the treatment conditions.

Statistics. Statistical analyses were performed with the aid of the Prism GraphPad software.

Results

Figure 6:
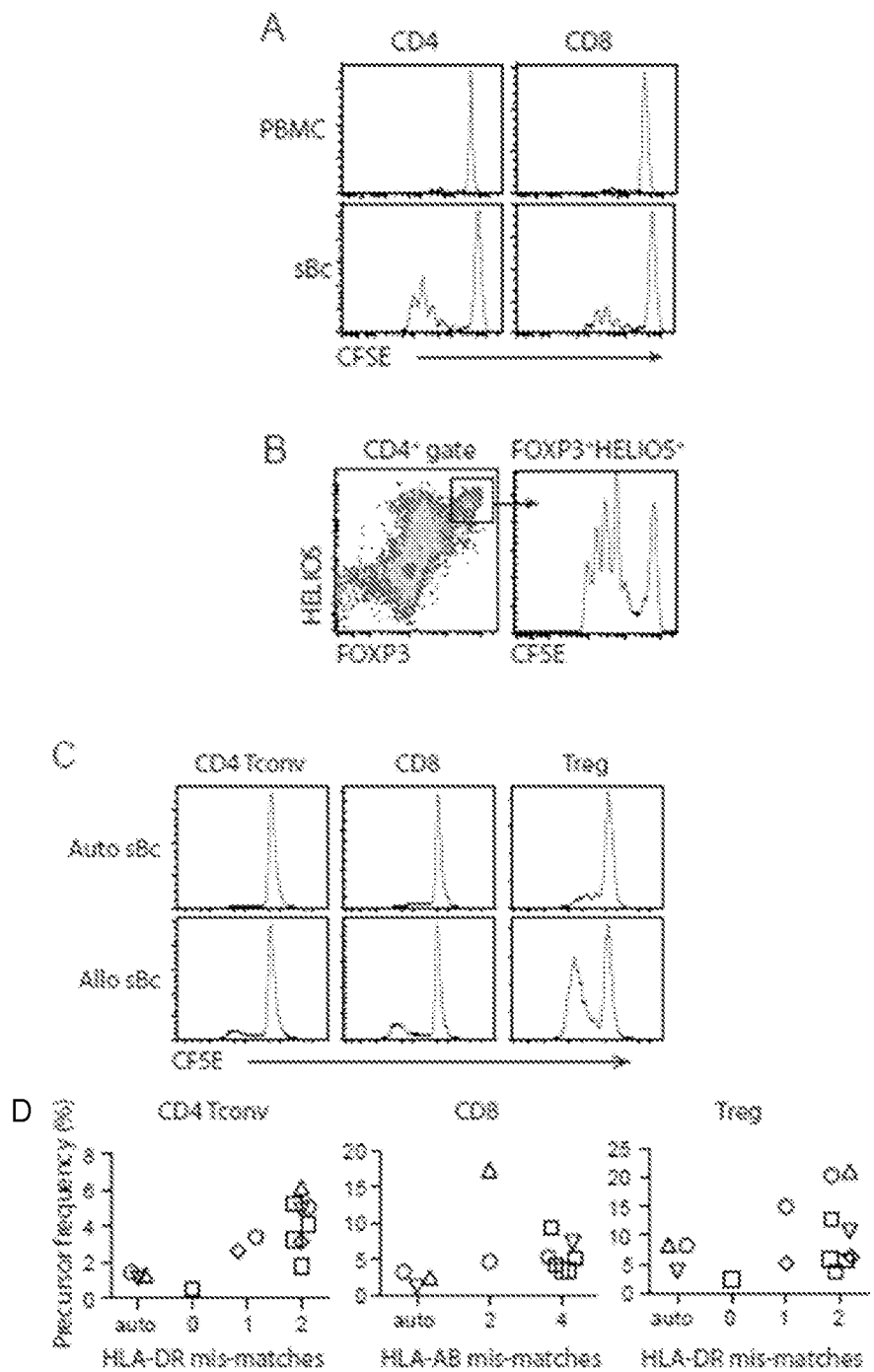
FIG. 6A and FIG. 6B shows PBMC and CD40L-sBc from the same donor compared for their ability to stimulate proliferation of alloreactive T cells in a one-way MLR. The responder PBMC were labeled with CFSE before MLR and the cultures were harvested on day 4 for flow cytometric analysis. Representative CFSE dilution profiles of CD4$^+$ and CD8$^+$ T cells (FIG. 6A) and CD4$^+$FOXP3$^+$HELIOS$^+$ Tregs (FIG. 6B) are shown. The data is a representative of at least 10 independent experiments.
FIG. 6C and FIG. 6D show autologous CD40L-sBc and allogeneic CD40L-sBc with different degree of HLA mis-matches with responder cells compared in their ability to stimulation proliferation of CD4$^+$ Tconv, CD8$^+$ T cells, and Treg cells. Each symbol represents the same responder. Results are a summary of 15 different stimulator and responder combinations.

CD40L-stimulated B cells are potent stimulators of alloantigen-reactive Tregs. Allogeneic PBMC, dendritic cells (DC), fresh B cells, and CD40L-stimulated B cells (referred as CD40L-sBc) have been used previously to selectively stimulate the expansion of human alloantigen-reactive cells[13-16]. However, less is known about the relative ability of these cell subsets in stimulating Tregs. A comparison of the relative potencies of irradiated PBMC, freshly isolated B cells, and CD40L-sBc in a one-way mixed lymphocyte reaction (MLR) demonstrated that CD40L-sBc were the most potent stimulators. Using a CFSE dye dilution assay to monitor CD4+ and CD8+ T cell proliferation, it was found that robust proliferative responses can be detected after 3.5 days of stimulation with CD40L-sBc and only a weak response was observed after stimulation using irradiated PBMCs (FIG. 6A). By further gating on CD4+FOXP3+ HELIOS+ Tregs, it was found that CD40L-sBc stimulated vigorous proliferation of Tregs in these MLR cultures (FIG. 6B). Freshly isolated peripheral blood B cells did not stimulate proliferation of T cells consistent with previous reports[23]. To determine if the proliferation was in response to alloantigens expressed on CD40L-sBc, the stimulatory capacity of autologous CD40L-sBc and allogeneic CD40L-sBc with varying degrees of HLA-mismatches to the responder T cells was compared. It was found that, for the same responding PBMC, the frequencies of responding CD4+ conventional T cells (Tconv) and Tregs positively correlated to the numbers of HLA-DR mismatches and frequencies of responding CD8+ T cells positively correlated with the numbers of HLA-AB mismatches (FIGS. 6C and 6D). Strikingly, frequencies of responding Tregs were consistently higher than those for CD4+ Tconv and CD8+ T cells. These results demonstrated that CD40L-sBc were potent stimulators of alloantigen-reactive Tregs and prompted the exploration of the utility of CD40L-sBc in selective expansion of alloantigen-reactive Tregs for clinical use.

Figure 7:
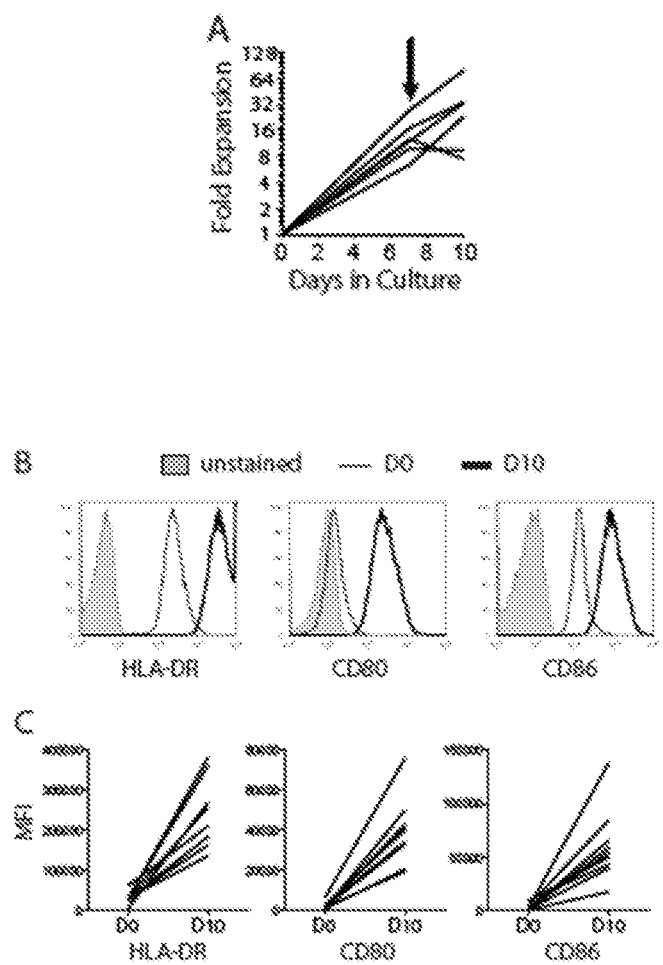
FIG. 7A shows the expansion of purified B cells in a 10-day culture. The arrow indicates the time of restimulation.
FIG. 7B and FIG. 7C show expression of HLA-DR, CD80, and CD86 in freshly isolated B cells and day 10 CD40L-sBc compared using flow cytometry. Sample overlay histograms are shown in FIG. 7B and charts summarizing results from independent experiments are shown in FIG. 7C. The data is summary of 6 independent experiments.

Generation of good manufacturing practice (GMP)-compliant CD40L-expressing feeder cells. A GMP-compatible human CD40L-expressing cell line, KT64-CD40L.HLADR0401 (abbreviated as K-CD40L) was generated to enable manufacture of Treg for clinical use. Lentiviral transduction was used to express CD40L in the myeloleukemia cell line K562, which has been used as vehicle for cancer vaccines and as artificial antigen presenting cells in manufacturing therapeutic T cells for clinical applications[24-27]. The expression of CD40L is essential to the generation of CD40L-sBc. CD64 and HLADR0401 expression does not interfere with CD40L activity while allowing for the cell line to be used for other applications including antigen-specific and polyclonal T cell expansions. Two rounds of stimulation with the K-CD40L cells on days 0 and 7 along with a constant supply of IL-4 led to 10 to 50 fold expansion of B cells purified from peripheral blood or spleens (FIG. 7A). When compared with freshly isolated B cells, the CD40L-sBc expressed significantly higher amounts of HLADR, CD80, and CD86 (FIGS. 7B and 7C), consistent with their enhanced potency in stimulating allogeneic T cells. Although there was consistent increase of HLA-DR, CD80, and CD86 expression on CD40L-sBc, the levels varied from donor to donor. However, CD40L-sBc generated from multiple donors were able to induce MLR and Treg expansion, suggesting that the potency of the CD40L-sBC was not strictly correlated with the absolute levels of the co-stimulatory and MHC class II molecules as long as a threshold was met.

CD40L-sBc robustly induce expansion of alloantigen-reactive Tregs. The conditions for optimal stimulation of alloantigen-reactive Tregs using CD40L-sBc were tested. A protocol for polyclonal expansion of Tregs using two round stimulations (days 0 and 9) of fluorescence-activated cell sorting (FACS) purified $CD4^+CD127^{lo/-}CD25^+$ Tregs with anti-CD3 and anti-CD28-coated beads is known[28]. For expanding alloantigen-reactive Tregs, a similar protocol was followed, but the beads were replaced with irradiated CD40L-sBc on days 0 and 9. A 50 to 300-fold expansion was achieved by day 14 using this protocol (FIG. 8A). At the end of the culture (day 14), the expanded Tregs were highly responsive to the same CD40L-sBc used to stimulate Treg expansion, but failed to respond to self CD40L-sBc (FIG. 8B). This result demonstrated a marked enrichment of Tregs reactive to the alloantigens expressed by the CD40L-sBc used to stimulate Treg expansion. In fact, by day 9 after the primary stimulation, the Tregs were already highly reactive to the CD40L-sBc, similar to that observed on day 14, suggesting that there might not be a need to further enrich for alloreactivity during restimulation. Given the robust expansion of PolyTreg using anti-CD3 and anti-CD28 stimulation[28] and the ease of standardization and implementation with bead-based protocols, replacing CD40L-sBc with anti-CD3 and anti-CD28-coated beads during restimulation may lead to comparable expansions. However, the results showed no significant differences in overall Treg expansions between sBc and bead restimulations (FIG. 8C). Therefore, the protocol of primary sBc stimulation followed by polyclonal restimulation with anti-CD3 and anti-CD28-coated beads was adopted.

Figure 8:
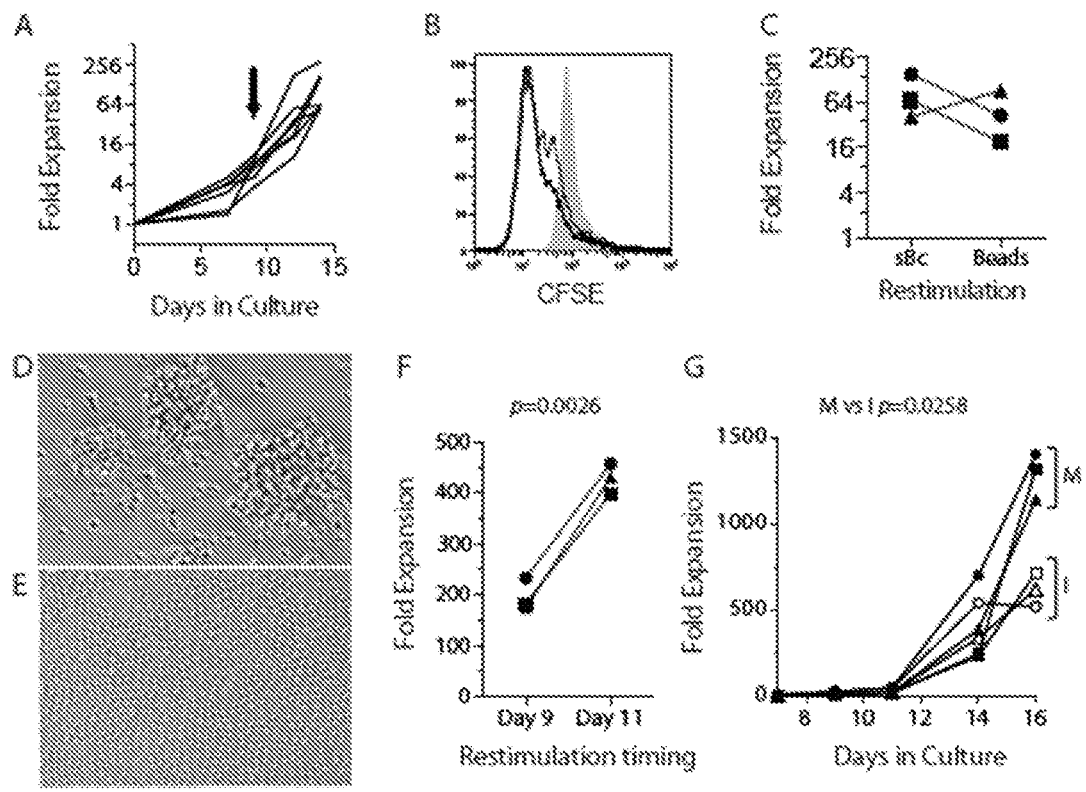
FIG. 8A shows allogeneic sBc used to stimulate FACS purified Tregs on day 0 and day 9. Fold expansion of Treg in the 14-day culture in 6 independent experiments is shown. The arrow indicates the time of restimulation.
FIG. 8B shows alloreactivity of expanded Tregs determined by labeling the expanded Tregs with CFSE before restimulation with the same CD40L-sBc used for expansion (thick line), anti-CD3 and anti-CD28-coated beads (thin line), or syngeneic CD40L-sBc (shaded histogram).
FIG. 8C shows Tregs stimulated with CD40L-sBc for 9 days and then split with half restimulated with CD40L-sBc from the same donor and the other half with anti-CD3 and anti-CD28-coated beads. Fold expansion on day 14 of three independent paired cultures is shown (p=0.52, two-tailed paired t test).
FIG. 8D and FIG. 8E show appearances of Treg cultures on days 9 (FIG. 8D) and 11 (FIG. 8E) after primary stimulation. Data represents results from at least 10 independent cultures.
FIG. 8F shows Tregs stimulated with CD40L-sBc for 9 or 11 days before restimulation with anti-CD3 and anti-CD28-coated beads. The cultures were harvested 5 days after restimulation and total fold expansion in 3 paired cultures are compared (p=0.0026, two-tailed paired t test).
FIG. 8G shows Tregs stimulated with CD40L-sBc for 11 days before restimulation with anti-CD3 and anti-CD28-coated beads from Invitrogen (open symbols) or Miltenyi Biotec (closed symbols). Cell expansions over time in 3 paired cultures are shown. Two-tailed paired t test was used to compare the difference in total fold expansion on day 16 (p=0.0258).

One unit of blood yields an average of 5 million Tregs after FACS purification. Therefore, using the protocol from FIG. 8, between 250 million to 1.5 billion alloantigen-reactive Tregs may be produced based on a 50- to 300-fold expansion. It was estimated that the numbers of Tregs needed for efficacy in transplantation in humans are in the range of 300 million to several billion cells[20]. To ensure consistent production of more than 300 million alloantigen-reactive Tregs, modified conditions to improve Treg expansion were explored. It was observed that, unlike the Poly-Tregs activated on day 0 with beads, the CD40L-sBc-stimulated Tregs continued to cluster and blast on day 9 after the initial stimulation (FIG. 8D). This observation suggested that the CD40L-sBc were more potent than mAb-coated beads leading to prolonged activation of the Tregs. Restimulation of activated T cells could lead to activation-induced cell death thus limiting optimal expansion. Therefore, restimulation was delayed until day 11 when the cells dissociated from the clusters and became smaller (FIG. 8E).

Delay restimulation significantly improved overall expansion (FIG. 8F). In addition to the timing of restimulation, it was found that the source of the beads used for restimulation greatly affected the rate of Treg expansion (FIG. 8G). Overall, by optimizing restimulation timing and restimulation reagents, the alloantigen-reactive Tregs routinely expanded 200 to 1600 fold, reliably producing more than $1 \times 10^9$ alloantigen-reactive Tregs in a 16-day period.

Figure 9:
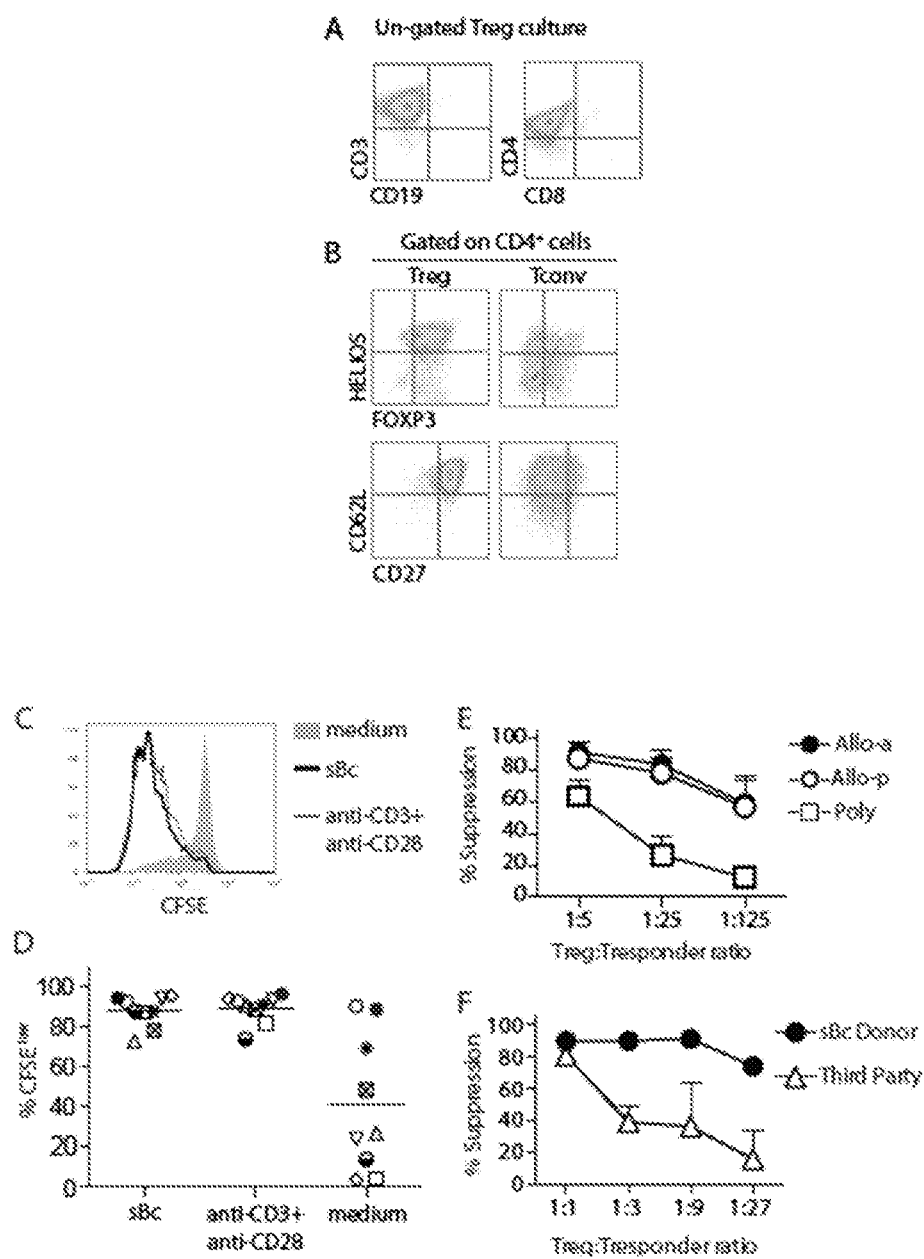
FIG. 9A and FIG. 9B show flow cytometric profiles of ungated (a) and CD4 gated (b) Treg cultures. Data are representative of at least 14 independent experiments. FIG.
FIG. 9D shows a summary of 7 independent cultures analyzed as described in FIG. 9C. Each symbol represents one independent Treg culture.
FIG. 9E shows a summary of in vitro suppression by Tregs expanded with two rounds of stimulation with allogeneic CD40L-sBc (closed circles, Allo-a, n=3), allogeneic sBc primary stimulation followed by polyclonal restimulation (open circles, Allo-p, n=8), or two rounds of polyclonal stimulations (open squares, Poly, n=5). Responders are PBMC from the Treg donor and stimulators are PBMC from the sBc donor. Data shown is mean+/−SEM suppression observed in 3 to 8 independent experiments. Two-way ANOVA with Bonferroni multiple comparison test was used to determine the statistical significance of the differences. Suppression at 1:5 ratio by different groups of Tregs are not significantly different. Suppression by PolyTregs is significantly lowered when compared to Allo-a Tregs ($p<0.001$ at 1:25 ratio and $p<0.01$ at 1:125 ratio), or when compared to Allo-p Tregs ($p<0.0001$ at 1:25 ratio and $p<0.001$ at 1:125 ratio). Allo-a and Allo-p Tregs are not significantly different from each other at all ratios).
FIG. 9F shows suppression by CD40L-sBc expanded Tregs stimulated by PBMC from the sBc donor (closed circles) or a third party donor (open triangles). Result shown is representative of two independent experiments.
Figure 10:
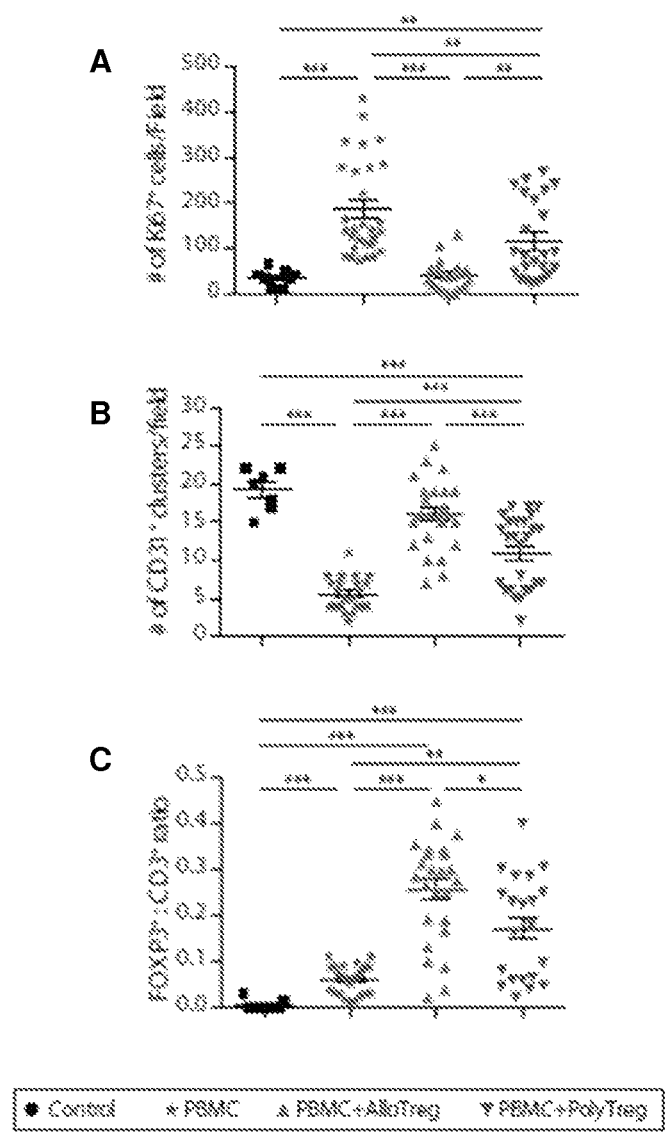
FIG. 10A, FIG. 10B and FIG. 10C show data from BALB/c.Rag2$^{-/-}$γc$^{-/-}$ mice transplanted with human skin and reconstituted with PBMC allogeneic to the skin donor. Immunofluorescence micrograph images were analyzed by counting 4 to 6 high-powered visual fields per stain for each graft. Quantitative results from four experimental groups were then compared. One-way ANOVA with Bonferroni multiple comparison test was used to determine the statistical significance of the differences.

In vitro characterization of CD40L-sBc-expanded Tregs. Tregs expanded with the CD40L-sBc protocol were found to be $CD3^+CD4^+$ with minimal contamination with $CD8^+$ T cell and $CD19^+$ B cells (FIG. 9A). The majority of the $CD4^+$ T cells were $FOXP3^+HELIOS^+$ and co-expressed CD27 and CD62L (FIG. 9B), distinct from the pattern expressed on similarly expanded Tconv cells (FIG. 9B). Lastly, the expanded Tregs had >80% demethylated Treg-specific demethylated region. Collectively, the phenotype of Tregs expanded using allogeneic CD40L-sBc suggested that they were stable committed Tregs.

To determine the reactivity of the expanded Tregs toward the allogeneic CD40L-sBc used for primary stimulation, Tregs harvested on day 16 were restimulated with the same CD40L-sBc. On average 87.5% (range 72.5 to 95.2%) of the alloantigen expanded Tregs proliferated in response to restimulation by the same sBc, similar to the proliferation induced using anti-CD3 and anti-CD28 beads (average 88.8%, range 73.6 to 96%), suggesting that the vast majority of the Tregs were reactive to the alloantigens expressed by the CD40L-sBc (FIGS. 9C and 9D).

Consistent with these phenotypic data and the enhanced alloantigen recognition, the expanded Tregs were highly suppressive when activated in vitro by PBMCs from the same donor as the CD40L-sBc (FIG. 9E). Side-by-side comparison of alloantigen-expanded Tregs and polyclonally expanded Tregs showed that the donor alloantigen-reactive Tregs were 5 to 25 fold more potent at suppressing MLR than PolyTregs (FIG. 9E). Treg expanded by restimulation with CD40L-sBc or anti-CD3 and anti-CD28 beads have identical activity in suppressing MLR (FIG. 9E), demonstrating that polyclonal restimulation did not alter their alloreactivity or suppressive activity in vivo. The suppressive activity stimulated by PBMC from the same donor of the CD40L-sBc or a third party donor was also compared. Tregs expanded with allogeneic sBc were 9 to 27 times more suppressive when stimulated by the relevant PBMC than when stimulated by third-party cells (FIG. 9F). Together, the results show that CD40L-sBc expanded Tregs had highly enriched reactivity and suppressive activity toward the alloantigens expressed by the B cells used for their expansion.

Figure 11:
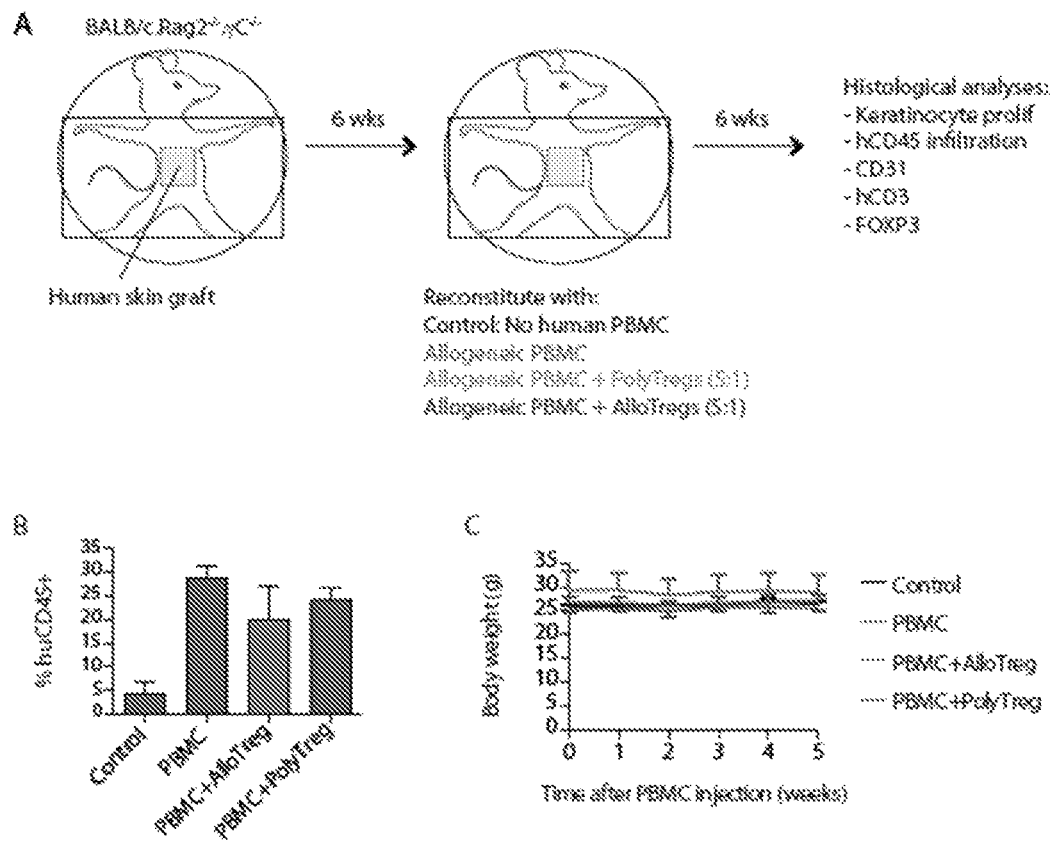
FIG. 11A is a schematic diagram of the experimental model and procedure is shown.
FIG. 11B shows PBMC reconstitution determined at the end of the experiment, demonstrating that co-infusion of Tregs did not significantly alter the extent of PBMC reconstitution.
FIG. 11C shows body weight of the BALB/c.Rag2$^{-/-}$γc$^{-/-}$ mice in four experimental groups was assessed to determine general health status, demonstrating that PBMC infusion did not induce graft-versus-host disease.
Figure 12:
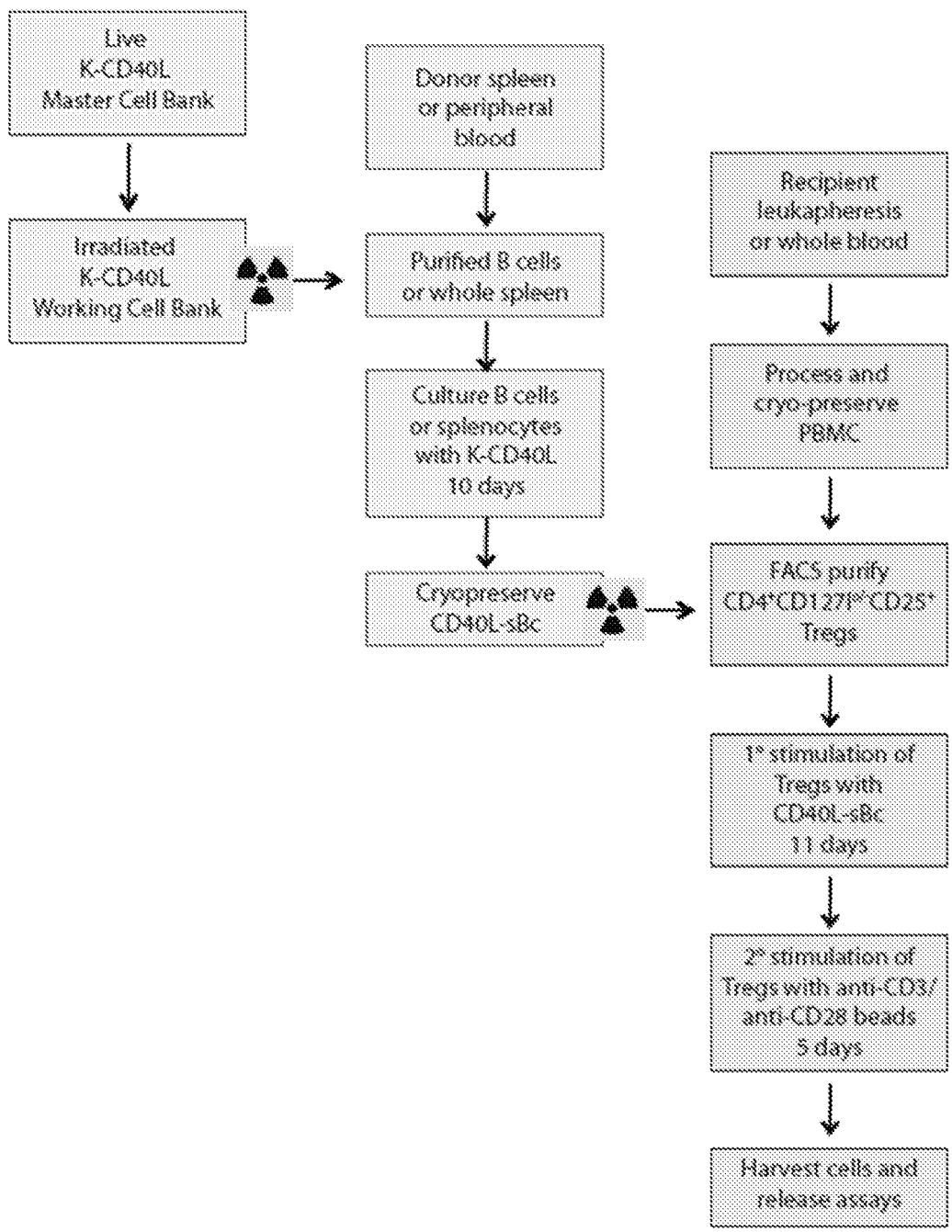
FIG. 12 is a schematic diagram of an exemplary alloantigen-reactive Treg manufacturing process.

Alloantigen-reactive Tregs are superior at protecting skin allografts in vivo. Using a model of alloimmune mediated injury of human skin allografts (FIG. 11A)[13], the protective function of alloantigen-reactive Tregs and PolyTregs was compared. $BALB/c.Rag2^{-/-}\gamma c^{-/-}$ mice were transplanted with human skin from a $HLA-DR0401^+$ donor and the grafts were allowed to heal for 6 weeks before adoptive transfer of allogeneic PBMC depleted of $CD25^+$ cells alone or in combination with different preparations of syngeneic Tregs at a ratio 5:1 effector cells:Treg cells. PBMC donors were $HLA-DR0401^-$ and alloantigen-reactive Tregs from these donors were expanded using $HLA-DR0401^+$ CD40L-sBc. Grafts were monitored until rejection or until up to a maximum of 6 weeks after PBMC reconstitution when the grafts were collected for histological analysis. Levels of human leukocyte engraftment in spleens were similar in the three groups of mice that received human PBMC alone or in combination with Tregs (FIG. 11B). No animal developed xenogeneic graft-versus-host disease symptoms confirmed by the maintenance of stable body weight (FIG. 11C).

Compared to the skin grafts in control animals that did not receive PBMC (Table 4-1), skin grafts in the PBMC alone group showed intense human CD45$^+$ mononuclear cell infiltrates at the dermo-epidermal junctions with concomitant increase in keratinocyte proliferation, loss of involucrin in the upper stratum spinosum and granulosum, and decreased vascularization as indicated by the reduction in clustered CD31$^+$ cells in the dermis (Table 4-1). These changes revealed active skin inflammation and loss of dermo-epidermal integrity mediated by the allogeneic human leukocytes. As reported in a previous study[13], all these inflammatory parameters in the grafts were reduced by co-injection of PolyTregs, correlating with an increase in FOXP3$^+$ cells (Table 4-1). Strikingly, skin grafts in mice that received alloantigen-reactive Tregs were nearly completely protected from histological features of graft injuries and were indistinguishable from those in control grafts except the infiltration of FOXP3$^+$ cells at the dermo-epidermal junctions (Table 4-1). Quantitative analysis of these histological findings demonstrated significant reduction in Ki67$^+$ keratinocytes, increase in CD31$^+$ vascular endothelial cells, correlating with significantly higher FOXP3$^+$ to CD3$^+$ cell ratios in grafts of mice injected with alloantigen-reactive Tregs when compared to those in mice treated with PolyTregs (Table 4-1). These results demonstrated that alloantigen-reactive Tregs were more effective at controlling allograft damage in vivo than the equivalent number of PolyTregs. At a ratio of 5:1 effector:Tregs, alloantigen-reactive Tregs completely protected the skin grafts from pathological changes induced by the effectors cells.

TABLE 4-1

Phenotype of Expanded Alloantigen-Reactive Tregs

| Marker | CD3+ | CD4+ | FOXP3+ | TSDR | HELIOS+ | CD62L+ CD27+ | CD8+ | CD19+ |
|---|---|---|---|---|---|---|---|---|
| Mean | 97.1 | 97.1 | 83.0 | 94.0 | 88.2 | 85.4 | 0.5 | 0.2 |
| SD | 2.6 | 1.9 | 10.8 | 15.5 | 6.6 | 6.4 | 0.2 | 0.2 |
| N | 14 | 14 | 14 | 10 | 14 | 10 | 14 | 14 |

Various modifications and variations of the present disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments. Indeed, various modifications of the described modes for carrying out the disclosure which are understood by those skilled in the art are intended to be within the scope of the claims.

REFERENCES

1. Wood, K. J. & Sakaguchi, S. Regulatory T cells in transplantation tolerance. *Nat Rev Immunol* 3, 199-210 (2003).
2. Walsh, P. T., Taylor, D. K. & Turka, L. A. Tregs and transplantation tolerance. *J Clin Invest* 114, 1398-1403 (2004).
3. Waldmann, H., Adams, E. & Cobbold, S. Reprogramming the immune system: co-receptor blockade as a paradigm for harnessing tolerance mechanisms. *Immunol Rev* 223, 361-370 (2008).
4. Tang, Q., Bluestone, J. A. & Kang, S. M. CD4(+)Foxp3(+) regulatory T cell therapy in transplantation. *J Mol Cell Biol* 4, 11-21 (2011).
5. Sakaguchi, S. Naturally arising Foxp3-expressing CD25+ CD4+ regulatory T cells in immunological tolerance to self and non-self. *Nat Immunol* 6, 345-352 (2005).
6. Sagoo, P., Lombardi, G. & Lechler, R. I. Regulatory T cells as therapeutic cells. *Curr Opin Organ Transplant* 13, 645-653 (2008).
7. Trzonkowski, P., et al. First-in-man clinical results of the treatment of patients with graft versus host disease with human ex vivo expanded CD4+CD25+CD127− T regulatory cells. *Clin Immunol* 133, 22-26 (2009).
8. Brunstein, C. G., et al. Infusion of ex vivo expanded T regulatory cells in adults transplanted with umbilical cord blood: safety profile and detection kinetics. *Blood* 117, 1061-1070 (2010).
9. Di Ianni, M., et al. Tregs prevent GVHD and promote immune reconstitution in HLA-haploidentical transplantation. *Blood* 117, 3921-3928 (2011).
10. Marek-Trzonkowska, N., et al. Administration of CD4+ CD25highCD127− Regulatory T Cells Preserves beta-Cell Function in Type 1 Diabetes in Children. *Diabetes Care* 35, 1817-1820 (2012).
11. Sanchez-Fueyo, A., et al. Specificity of CD4+CD25+ regulatory T cell function in alloimmunity. *J Immunol* 176, 329-334 (2006).
12. Tsang, J. Y., et al. Conferring indirect allospecificity on CD4+CD25+ Tregs by TCR gene transfer favors transplantation tolerance in mice. *J Clin Invest* 118, 3619-3628 (2008).
13. Sagoo, P., et al. Human regulatory T cells with alloantigen specificity are more potent inhibitors of alloimmune skin graft damage than polyclonal regulatory T cells. *Sci Transl Med* 3, 83ra42 (2011).
14. Peters, J. H., Hilbrands, L. B., Koenen, H. J. & Joosten, I. Ex vivo generation of human alloantigen-specific regulatory T cells from CD4(pos)CD25(high) T cells for immunotherapy. *PLoS One* 3, e2233 (2008).
15. Koenen, H. J., Fasse, E. & Joosten, I. CD27/CFSE-based ex vivo selection of highly suppressive alloantigen-specific human regulatory T cells. J Immunol 174, 7573-7583 (2005).
16. Banerjee, D. K., Dhodapkar, M. V., Matayeva, E., Steinman, R. M. & Dhodapkar, K. M. Expansion of FOXP3high regulatory T cells by human dendritic cells (DCs) in vitro and after injection of cytokine-matured DCs in myeloma patients. *Blood* 108, 2655-2661 (2006).
17. Tu, W., et al. Efficient generation of human alloantigen-specific CD4+ regulatory T cells from naive precursors by CD40-activated B cells. *Blood* 112, 2554-2562 (2008).
18. Koenen, H. J., et al. Human CD25highFoxp3pos regulatory T cells differentiate into IL-17-producing cells. *Blood* 112, 2340-2352 (2008).

19. Baron, U., et al. DNA demethylation in the human FOXP3 locus discriminates regulatory T cells from activated FOXP3(+) conventional T cells. *Eur J Immunol* 37, 2378-2389 (2007).
20. Tang, Q. & Lee, K. Regulatory T-cell therapy for transplantation: how many cells do we need? *Curr Opin Organ Transplant* 17, 349-354 (2012).
21. Hoffmann, P., et al. Loss of FOXP3 expression in natural human CD4+CD25+ regulatory T cells upon repetitive in vitro stimulation. *Eur J Immunol* 39, 1088-1097 (2009).
22. Hippen, K. L., et al. Massive ex vivo expansion of human natural regulatory T cells (T(regs)) with minimal loss of in vivo functional activity. *Sci Transl Med* 3, 83ra41 (2011).
23. Chen, L. C., Delgado, J. C., Jensen, P. E. & Chen, X. Direct expansion of human allospecific FoxP3+CD4+ regulatory T cells with allogeneic B cells for therapeutic application. *J Immunol* 183, 4094-4102 (2009).
24. Ye, Q., et al. Engineered artificial antigen presenting cells facilitate direct and efficient expansion of tumor infiltrating lymphocytes. *Journal of translational medicine* 9, 131 (2011).
25. Butler, M. O., et al. Establishment of antitumor memory in humans using in vitro-educated CD8+ T cells. *Sci Transl Med* 3, 80ra34 (2011).
26. Smith, B. D., et al. K562/GM-CSF immunotherapy reduces tumor burden in chronic myeloid leukemia patients with residual disease on imatinib mesylate. *Clin Cancer Res* 16, 338-347 (2010).
27. Borrello, I. M., et al. Granulocyte-macrophage colony-stimulating factor (GM-CSF)-secreting cellular immunotherapy in combination with autologous stem cell transplantation (ASCT) as postremission therapy for acute myeloid leukemia (AML). *Blood* 114, 1736-1745 (2009).
28. Putnam, A. L., et al. Expansion of human regulatory T-cells from patients with type 1 diabetes. *Diabetes* 58, 652-662 (2009).
29. Golovina, T. N., et al. CD28 costimulation is essential for human T regulatory expansion and function. *J Immunol* 181, 2855-2868 (2008).
30. Cobbold, S. & Waldmann, H. Infectious tolerance. *Curr Opin Immunol* 10, 518-524 (1998).
31. Kendal, A. R., et al. Sustained suppression by Foxp3+ regulatory T cells is vital for infectious transplantation tolerance. *J Exp Med* 208, 2043-2053 (2011).
32. Sagoo, P., Lombardi, G. & Lechler, R. I. Relevance of regulatory T cell promotion of donor-specific tolerance in solid organ transplantation. *Frontiers in immunology* 3, 184 (2012).
33. Novak, E. J., Liu, A. W., Nepom, G. T. & Kwok, W. W. MHC class II tetramers identify peptide-specific human CD4(+) T cells proliferating in response to influenza A antigen. *J Clin Invest* 104, R63-67 (1999).
34. Parry, R. V., Rumbley, C. A., Vandenberghe, L. H., June, C. H. & Riley, J. L. CD28 and inducible costimulatory protein Src homology 2 binding domains show distinct regulation of phosphatidylinositol 3-kinase, Bcl-xL, and IL-2 expression in primary human CD4 T lymphocytes. *J Immunol* 171, 166-174 (2003).
35. Suhoski, M. M., et al. Engineering artificial antigen-presenting cells to express a diverse array of co-stimulatory molecules. *Molecular therapy: the journal of the American Society of Gene Therapy* 15, 981-988 (2007).
36. Zand, M. S., et al. A renewable source of donor cells for repetitive monitoring of T- and B-cell alloreactivity. *Am J Transplant* 5, 76-86 (2005).
37. Wieczorek, G., et al. Quantitative DNA methylation analysis of FOXP3 as a new method for counting regulatory T cells in peripheral blood and solid tissue. *Cancer Res* 69, 599-608 (2009).

We claim:

1. A method for the production of human, donor-reactive regulatory T cells (Tregs), comprising:
    a) co-culturing CD19+ B cells of a human donor with irradiated CD40L+ human leukemia feeder cells under conditions effective in producing stimulated B cells (sBc);
    b) co-culturing CD4+, CD25+, CD127−/lo T cells isolated from peripheral blood mononuclear cells (PBMC) of a human recipient with said sBc under conditions effective in selectively expanding human donor-reactive regulatory T cells (Tregs); and
    c) re-stimulating said donor-reactive Tregs by cross-linking CD3 and CD28 of said donor-reactive Tregs using monoclonal antibodies under conditions effective in producing re-stimulated donor-reactive Tregs that are CD4+, Helios+ and Foxp3+,
    wherein the donor is a first human subject and the recipient is a second human subject and the donor is HLA-mismatched in relation to the human recipient.
2. The method of claim 1, wherein the HLA-mismatch comprises a mismatch at one, two, three or four of HLA-A, HLA-B, HLA-C and HLA-DR.
3. The method of claim 1, wherein step c) commences 9-12days after step b) commences.
4. The method of claim 1, wherein said restimulated donor-reactive Tregs are CD27+, CD62L+.
5. The method of claim 1, wherein said CD4+, CD25+, CD127−/lo T cells were isolated by fluorescent activated cell sorting (FACS) from cryopreserved peripheral blood mononuclear cells (PBMC) obtained from said human recipient.
6. The method of claim 1, wherein step a) comprises co-culturing said B cells and said feeder cells in medium comprising insulin, transferrin, interleukin-4 and cyclosporine A.
7. The method of claim 1, wherein step b) comprises co-culturing said sBc and said CD4+, CD25+, CD127−/lo T cells in medium comprising interleukin-2 after said sBc have been irradiated.
8. The method of claim 1, wherein said re-stimulated donor-reactive Tregs comprise 200 fold to 2000 fold more cells than said CD4+, CD25+, CD127−/lo T cells at the onset of step b).
9. The method of claim 1, wherein the restimulated donor-reactive Tregs have a Foxp3 promoter with a demethylated Treg-specific demethylation region.

* * * * *

UNITED STATES PATENT AND TRADEMARK OFFICE
CERTIFICATE OF CORRECTION

| | |
|---|---|
| PATENT NO. | : 9,801,911 B2 |
| APPLICATION NO. | : 14/382537 |
| DATED | : October 31, 2017 |
| INVENTOR(S) | : Qizhi Tang et al. |

Page 1 of 1

It is certified that error appears in the above-identified patent and that said Letters Patent is hereby corrected as shown below:

In the Specification

In Column 1, Line 16, delete "P30 DK063720" and insert -- Grant Nos. P30 DK063720 and AI095135 --.

In the Claims

In Column 24, Claim 3, Line 36, delete "9-12days" and insert -- 9-12 days --.

Signed and Sealed this
Twenty-fifth Day of December, 2018

Andrei Iancu
*Director of the United States Patent and Trademark Office*